United States Patent

Penny et al.

(10) Patent No.: US 8,426,822 B1
(45) Date of Patent: Apr. 23, 2013

(54) SYSTEM AND METHOD FOR THREE-DIMENSIONAL IMAGING USING SCATTERING FROM ANNIHILATION COINCIDENCE PHOTONS

(71) Applicants: Robert David Penny, San Diego, CA (US); John D. Valentine, San Diego, CA (US)

(72) Inventors: Robert David Penny, San Diego, CA (US); John D. Valentine, San Diego, CA (US)

(73) Assignee: Science Application International Corporation, McLean, VA (US)

( * ) Notice: Subject to any disclaimer, the term of this patent is extended or adjusted under 35 U.S.C. 154(b) by 0 days.

(21) Appl. No.: 13/646,920

(22) Filed: Oct. 8, 2012

Related U.S. Application Data

(63) Continuation of application No. 12/939,449, filed on Nov. 4, 2010, now Pat. No. 8,314, 394.

(60) Provisional application No. 61/257,874, filed on Nov. 4, 2009.

(51) Int. Cl.
G01T 1/164 (2006.01)
(52) U.S. Cl.
USPC .................................................. 250/363.03
(58) Field of Classification Search .................. 250/362, 250/363.01–363.1
See application file for complete search history.

(56) References Cited

U.S. PATENT DOCUMENTS 3,124,679 A    3/1964  Tittman et al. ............... 250/43.5
3,240,971 A    3/1966  Morgan ........................ 376/153
3,390,269 A    6/1968  Packard ........................ 250/328
3,670,164 A    6/1972  Hardy et al. .................. 250/366
3,780,291 A    12/1973 Stein et al. .................... 250/363
3,784,827 A    1/1974  Calhoun ..................... 250/106 S
3,790,785 A    2/1974  Paolini et al. ............. 250/71.5 R
3,808,444 A    4/1974  Schneeberger et al. ....... 250/492
3,829,695 A    8/1974  Powell ....................... 250/358.1
3,835,324 A    9/1974  Weigle .......................... 250/360
3,984,332 A    10/1976 Nelson et al. ................. 250/368

(Continued)

FOREIGN PATENT DOCUMENTS

EP    0 059 382    8/1985
EP    0 491 977    6/1994

(Continued)

OTHER PUBLICATIONS

U.S. Appl. No. 90/005,268, filed Feb. 19, 1999.

(Continued)

Primary Examiner — Kiho Kim
(74) Attorney, Agent, or Firm — King & Spaulding LLP

(57) ABSTRACT

Systems and methods are described herein for performing three-dimensional imaging using backscattered photons generated from a positron-electron annihilation. The systems and methods are implemented using the pair of photons created from a positron-electron annihilation. The trajectory and emission time of one of the photons is detected near the annihilation event. Using this collected data, the trajectory of the second photon can be determined. The second photon is used as a probe photon and is directed towards a target for imaging. The interaction of the second probe photon with the target produces back scattered photons that can be detected and used to create a three-dimensional image of the target. The systems and methods described herein are particularly advantageous because they permit imaging with a system from a single side of the target, as opposed to requiring imaging equipment on both sides of the target.

16 Claims, 10 Drawing Sheets

U.S. PATENT DOCUMENTS

| | | | |
|---|---|---|---|
| 3,997,787 A | 12/1976 | Fearon et al. | 250/359 |
| 4,047,036 A | 9/1977 | Smith et al. | 378/56 |
| 4,064,440 A | 12/1977 | Roder | 250/359 |
| 4,115,696 A | 9/1978 | Truscott | 378/13 |
| 4,173,010 A | 10/1979 | Hoffmann | 340/937 |
| 4,179,100 A | 12/1979 | Sashin et al. | 250/370.09 |
| 4,229,654 A | 10/1980 | Arya et al. | 250/358 R |
| 4,251,726 A | 2/1981 | Alvarez | 250/302 |
| 4,255,659 A | 3/1981 | Kaufman et al. | 250/370 |
| 4,366,382 A | 12/1982 | Kotowski | 378/57 |
| 4,394,576 A | 7/1983 | Tanaka et al. | 250/366 |
| 4,430,568 A | 2/1984 | Yoshida et al. | 250/358.1 |
| 4,454,606 A | 6/1984 | Relihan | 378/97 |
| 4,502,147 A | 2/1985 | Michaels | 378/206 |
| 4,531,058 A | 7/1985 | Burnham et al. | 250/363.03 |
| 4,558,220 A | 12/1985 | Evans | 250/269.3 |
| 4,566,113 A | 1/1986 | Donges et al. | 378/57 |
| 4,598,202 A | 7/1986 | Koechner | 250/366 |
| 4,599,740 A | 7/1986 | Cable | 378/57 |
| 4,626,688 A | 12/1986 | Barnes | 250/361 R |
| 4,649,276 A | 3/1987 | Suzuki | 250/370.11 |
| 4,651,005 A | 3/1987 | Baba et al. | 250/360.1 |
| 4,697,594 A | 10/1987 | Mayo, Jr. | 128/653 |
| 4,743,764 A | 5/1988 | Casey et al. | 250/363.03 |
| 4,749,863 A | 6/1988 | Casey et al. | 250/363.03 |
| 4,750,972 A | 6/1988 | Casey et al. | 216/24 |
| 4,755,680 A | 7/1988 | Logan | 250/363.01 |
| 4,817,123 A | 3/1989 | Sones et al. | 378/98 |
| 4,819,256 A | 4/1989 | Annis et al. | 378/87 |
| 4,825,454 A | 4/1989 | Annis | 378/87 |
| 4,857,748 A | 8/1989 | Takiguchi | 250/559.21 |
| 4,873,708 A | 10/1989 | Cusano et al. | 378/19 |
| 4,893,015 A | 1/1990 | Kubierschky et al. | 250/369 |
| 4,924,098 A | 5/1990 | Wasserman | 250/380 |
| 4,933,961 A | 6/1990 | Rushbrooke et al. | 378/57 |
| 4,946,256 A | 8/1990 | Woodruff | 359/230 |
| 4,951,201 A | 8/1990 | Takeo et al. | 382/128 |
| 4,963,746 A | 10/1990 | Morgan et al. | 250/363.02 |
| 4,973,846 A | 11/1990 | Lanza et al. | 250/385.1 |
| 4,987,581 A | 1/1991 | Bernardi | 378/19 |
| 4,989,229 A | 1/1991 | Negrelli et al. | 378/198 |
| 5,014,293 A | 5/1991 | Boyd et al. | 378/197 |
| 5,022,062 A | 6/1991 | Annis | 378/86 |
| 5,065,418 A | 11/1991 | Bermbach et al. | 378/57 |
| 5,091,650 A | 2/1992 | Uchida et al. | 250/366 |
| 5,091,924 A | 2/1992 | Bermbach et al. | 378/57 |
| 5,098,640 A | 3/1992 | Gozani et al. | 376/166 |
| 5,115,394 A | 5/1992 | Walters | 382/131 |
| 5,151,588 A | 9/1992 | Kiri et al. | 250/208.1 |
| 5,179,581 A | 1/1993 | Annis | 378/57 |
| 5,200,626 A | 4/1993 | Schultz et al. | 250/390.04 |
| 5,210,420 A | 5/1993 | Hartz et al. | 250/363.03 |
| 5,218,533 A | 6/1993 | Schanen | 378/9 |
| 5,237,598 A | 8/1993 | Albert | 378/99 |
| 5,243,664 A | 9/1993 | Tuy | 382/130 |
| 5,247,561 A | 9/1993 | Kotowski | 378/87 |
| 5,253,282 A | 10/1993 | Pelc | 378/98.2 |
| 5,287,396 A | 2/1994 | Stegehuis | 378/98.2 |
| 5,300,782 A | 4/1994 | Johnston et al. | 250/363.03 |
| 5,339,350 A | 8/1994 | Thelosen | 378/198 |
| 5,379,334 A | 1/1995 | Zimmer et al. | 378/98.2 |
| 5,379,336 A | 1/1995 | Kramer et al. | 378/98.8 |
| 5,453,623 A | 9/1995 | Wong et al. | 250/363.03 |
| 5,464,013 A | 11/1995 | Lemelson | 128/653.1 |
| 5,465,284 A | 11/1995 | Karellas | 378/62 |
| 5,481,584 A | 1/1996 | Tang et al. | 378/98.9 |
| 5,483,569 A | 1/1996 | Annis | 378/87 |
| 5,493,517 A | 2/1996 | Frazier | 364/564 |
| 5,493,596 A | 2/1996 | Annis | 378/57 |
| 5,524,133 A | 6/1996 | Neale et al. | 378/53 |
| 5,541,856 A | 7/1996 | Hammermeister | 364/552 |
| 5,585,603 A | 12/1996 | Vogeley, Jr. | 177/25.13 |
| 5,586,162 A | 12/1996 | Grichnik | 378/198 |
| 5,591,967 A | 1/1997 | Moake | 250/252.1 |
| 5,629,669 A | 5/1997 | Asano et al. | 340/436 |
| 5,638,420 A | 6/1997 | Armistead | 378/57 |
| 5,642,393 A | 6/1997 | Krug et al. | 378/57 |
| 5,642,394 A | 6/1997 | Rothschild | 378/57 |
| 5,661,774 A | 8/1997 | Gordon et al. | 378/101 |
| 5,668,847 A | 9/1997 | Hernandez | 378/65 |
| 5,679,956 A | 10/1997 | Johnston | 250/357.1 |
| 5,687,210 A | 11/1997 | Maitrejean et al. | 378/57 |
| 5,692,028 A | 11/1997 | Geus | 378/57 |
| 5,698,854 A | 12/1997 | Gupta | 250/358.1 |
| 5,706,326 A | 1/1998 | Gard | 378/19 |
| 5,712,926 A | 1/1998 | Eberhard et al. | 382/205 |
| 5,754,617 A | 5/1998 | Itoh | 378/4 |
| 5,764,683 A | 6/1998 | Swift et al. | 378/57 |
| 5,771,272 A | 6/1998 | Berger et al. | 378/207 |
| 5,797,396 A | 8/1998 | Geiser et al. | 600/407 |
| 5,834,780 A | 11/1998 | Morgan et al. | 250/363.04 |
| 5,835,558 A | 11/1998 | Maschke | 378/198 |
| 5,835,561 A | 11/1998 | Moorman et al. | 378/98 |
| 5,838,759 A | 11/1998 | Armistead | 378/57 |
| 5,870,449 A | 2/1999 | Lee et al. | 378/57 |
| 5,903,623 A | 5/1999 | Swift et al. | 378/57 |
| 5,910,973 A | 6/1999 | Grodzins | 378/57 |
| 5,936,249 A | 8/1999 | Eisen et al. | 250/370.06 |
| 5,986,266 A | 11/1999 | Andreaco et al. | 250/363.09 |
| 5,986,275 A | 11/1999 | Teates | 250/498.1 |
| 6,026,143 A | 2/2000 | Simanovsky et al. | 378/57 |
| 6,031,890 A | 2/2000 | Bermbach et al. | 378/57 |
| 6,058,158 A | 5/2000 | Eiler | 378/57 |
| 6,081,580 A | 6/2000 | Grodzins et al. | 378/87 |
| 6,094,468 A | 7/2000 | Wilting et al. | 378/8 |
| 6,122,344 A | 9/2000 | Beevor | 378/88 |
| 6,151,381 A | 11/2000 | Grodzins et al. | 378/90 |
| 6,188,473 B1 | 2/2001 | Leistner et al. | 356/213 |
| 6,249,567 B1 | 6/2001 | Rothschild et al. | 378/88 |
| 6,252,929 B1 | 6/2001 | Swift et al. | 378/57 |
| 6,255,654 B1 | 7/2001 | Verbinski et al. | 250/358.1 |
| 6,269,142 B1 | 7/2001 | Smith | 378/57 |
| 6,271,510 B1 | 8/2001 | Boxen | 250/208.1 |
| 6,282,258 B1 | 8/2001 | Stein et al. | 378/54 |
| 6,282,260 B1 | 8/2001 | Grodzins | 378/87 |
| 6,292,533 B1 | 9/2001 | Switft et al. | 378/57 |
| 6,320,193 B1 | 11/2001 | Morrison et al. | 250/393 |
| 6,320,933 B1 | 11/2001 | Grodzins et al. | 378/89 |
| 6,347,132 B1 | 2/2002 | Annis | 378/57 |
| 6,362,479 B1 | 3/2002 | Andreaco et al. | 250/366 |
| 6,380,540 B1 | 4/2002 | Maor et al. | 250/363.04 |
| 6,385,288 B1 | 5/2002 | Kanematsu | 378/65 |
| 6,389,108 B1 | 5/2002 | Ein-Gal | 378/147 |
| 6,400,795 B2 | 6/2002 | Yagi | 378/45 |
| 6,424,695 B1 | 7/2002 | Grodzins et al. | 378/87 |
| 6,459,764 B1 | 10/2002 | Chalmers et al. | 378/88 |
| 6,473,487 B1 | 10/2002 | Le | 378/57 |
| 6,507,025 B1 | 1/2003 | Verbinski et al. | 250/358.1 |
| 6,507,642 B2 | 1/2003 | Fujishige et al. | 378/151 |
| 6,542,580 B1 | 4/2003 | Carver et al. | 378/57 |
| 6,552,346 B2 | 4/2003 | Verbinski et al. | 250/358.1 |
| 6,574,302 B2 | 6/2003 | Adriaansz | 378/54 |
| 6,597,759 B2 | 7/2003 | Mazess et al. | 378/53 |
| 6,605,809 B1 | 8/2003 | Engels et al. | 250/394 |
| 6,621,891 B2 | 9/2003 | Danielsson | 378/150 |
| 6,636,581 B2 | 10/2003 | Sorenson | 378/58 |
| 6,637,266 B1 | 10/2003 | Froom | 73/583 |
| 6,644,853 B1 | 11/2003 | Kantor et al. | 378/203 |
| 6,649,906 B2 | 11/2003 | Adolph et al. | 250/269.1 |
| 6,727,506 B2 | 4/2004 | Mallette | 250/394 |
| 6,757,008 B1 | 6/2004 | Smith | 348/143 |
| 6,768,421 B1 | 7/2004 | Alioto et al. | 340/600 |
| 6,785,357 B2 | 8/2004 | Bernardi et al. | 378/57 |
| 6,788,761 B2 | 9/2004 | Bijjani et al. | 378/57 |
| 6,843,599 B2 | 1/2005 | Le et al. | 378/198 |
| 6,920,197 B2 | 7/2005 | Kang et al. | 378/57 |
| 6,922,461 B2 | 7/2005 | Kang et al. | 378/57 |
| 6,928,141 B2 | 8/2005 | Carver et al. | 378/57 |
| 7,039,159 B2 | 5/2006 | Muenchau et al. | 378/57 |
| 7,045,787 B1 | 5/2006 | Verbinski et al. | 250/358.1 |
| 7,045,788 B2 | 5/2006 | Iwatschenko-Borho et al. | 250/359.1 |
| 7,046,768 B1 | 5/2006 | Gilevich | 378/160 |
| 7,084,901 B2 | 8/2006 | Smith | 348/143 |
| 7,099,434 B2 | 8/2006 | Adams et al. | 378/57 |
| 7,103,137 B2 | 9/2006 | Seppi et al. | 378/9 |
| RE39,396 E | 11/2006 | Swift et al. | 378/57 |

| | | | |
|---|---|---|---|
| 7,133,491 B2 | 11/2006 | Bernardi et al. | 378/57 |
| 7,215,738 B2 | 5/2007 | Muenchau et al. | 378/57 |
| 7,218,704 B1 | 5/2007 | Adams et al. | 378/57 |
| 7,336,767 B1 | 2/2008 | Le | 378/147 |
| 7,336,768 B2 | 2/2008 | Ogawa | 378/156 |
| 7,352,843 B2 | 4/2008 | Hu et al. | 378/57 |
| 7,352,844 B1 | 4/2008 | Muenchau et al. | 378/57 |
| 7,366,282 B2 | 4/2008 | Peschmann | 378/57 |
| 7,379,530 B2 | 5/2008 | Hoff et al. | 378/57 |
| 7,386,092 B2 | 6/2008 | Kang et al. | 378/57 |
| 7,397,891 B2 | 7/2008 | Johnson et al. | 378/57 |
| 7,405,409 B2 | 7/2008 | Kearfott | 250/390.04 |
| 7,408,160 B2 | 8/2008 | Verbinski et al. | 250/358.1 |
| 7,453,987 B1 | 11/2008 | Richardson | 378/98.9 |
| 7,463,715 B2 | 12/2008 | Spahn | 378/98.12 |
| 7,483,510 B2 | 1/2009 | Carver et al. | 378/57 |
| 7,483,518 B2 | 1/2009 | Hamill | 378/144 |
| 7,486,768 B2 | 2/2009 | Allman et al. | 378/57 |
| 7,486,769 B2 | 2/2009 | Brondo, Jr. | 378/57 |
| 7,505,556 B2 | 3/2009 | Chalmers et al. | 378/57 |
| 7,526,064 B2 | 4/2009 | Akery | 378/57 |
| 7,551,715 B2 | 6/2009 | Rothschild et al. | 378/57 |
| 7,555,099 B2 | 6/2009 | Rothschild et al. | 378/90 |
| 7,592,597 B2 * | 9/2009 | Hefetz et al. | 250/363.1 |
| 7,803,103 B2 | 9/2010 | Hillstead et al. | 600/7 |
| 8,183,531 B2 * | 5/2012 | Chinn et al. | 250/363.04 |
| 2002/0070365 A1 | 6/2002 | Karellas | 250/581 |
| 2002/0090050 A1 | 7/2002 | Nutt et al. | 378/19 |
| 2002/0094064 A1 | 7/2002 | Zhou et al. | 378/122 |
| 2002/0134942 A1 * | 9/2002 | Pehl et al. | 250/369 |
| 2002/0136353 A1 | 9/2002 | Kang et al. | 378/57 |
| 2003/0174221 A1 | 9/2003 | Tsuda | 348/241 |
| 2004/0086078 A1 | 5/2004 | Adams et al. | 378/57 |
| 2004/0109532 A1 | 6/2004 | Ford et al. | 378/57 |
| 2004/0256565 A1 | 12/2004 | Adams et al. | 250/358.1 |
| 2005/0029460 A1 | 2/2005 | Iwatschenko-Borho et al. | 250/359.1 |
| 2005/0031293 A1 | 2/2005 | Kim et al. | 385/146 |
| 2005/0084073 A1 | 4/2005 | Seppi et al. | 378/57 |
| 2005/0105665 A1 | 5/2005 | Grodzins et al. | 376/157 |
| 2006/0140341 A1 | 6/2006 | Carver et al. | 378/57 |
| 2007/0064868 A1 | 3/2007 | Kostka et al. | 378/53 |
| 2007/0140423 A1 | 6/2007 | Foland | 378/57 |
| 2008/0224050 A1 * | 9/2008 | Thielemans et al. | 250/362 |
| 2008/0292050 A1 | 11/2008 | Goodenough et al. | 378/57 |
| 2009/0074142 A1 | 3/2009 | Bertozzi et al. | 378/88 |
| 2009/0147913 A1 | 6/2009 | Dragon et al. | 378/57 |
| 2009/0257555 A1 | 10/2009 | Chalmers et al. | 378/57 |

FOREIGN PATENT DOCUMENTS

| | | |
|---|---|---|
| GB | 1 227 435 | 4/1971 |
| GB | 2158572 | 11/1985 |
| GB | 2 277 013 A | 10/1994 |
| JP | 58-216974 | 12/1983 |
| JP | 62-129776 | 6/1987 |
| JP | 62-135787 | 6/1987 |

OTHER PUBLICATIONS

U.S. Appl. No. 07/782,970, filed Oct. 25, 1991, Annis.

International Search Report and Written Opinion for Application No. PCT/US2009/038903, 10 pp., dated Dec. 1, 2009 (mailing date). Date Considered: Nov. 30, 2011.

SAIC: News Release dated Aug. 25, 2004, http://www.saic.com/news/2004/aug/25.html (2pp).

"Mobile VACIS® Inspection System, Technical Specifications" [online], [retrieved on Jul. 8, 2004], 4 pp., Retrieved from the Internet: http://www.saic.com/products/security/mobile-vacis/mobile-tech.html.

"Pallet VACIS® Inspection System, Technical Specifications" [online], [retrieved on Jul. 8, 2004], 2 pp., Retrieved from the Internet: http://www.saic.com/products/security/pallet-vacis/pallet-tech.html.

"Pallet VACIS® Inspection System, Technical Specifications" [online], [retrieved on Jul. 8, 2004], 3 pp., Retrieved from the Internet: http://www.saic.com/products/security/portal-vacis/portal-vacis-tech.html.

"Railroad VACIS® Inspection System, Technical Specifications" [online], [retrieved on Jul. 8, 2004], 3 pp., Retrieved from the Internet: http://www.saic.com/products/security/rr-vacis/railroad-tech.html.

"Relocatable VACIS® Inspection System, Technical Specifications" [online], [retrieved on Jul. 8, 2004], 3 pp., Retrieved from the Internet: http://www.saic.com/products/security/relocatable-vacis/relocatable-vacis-tech.html.

"VACIS® Inspection Systems Combat Contraband Transport" [online], [retrieved on Jul. 8, 2004], 2 pp., Retrieved from the Internet: http://www.saic.com/cover-archive/transport/VACIS.html.

"SAIC Mobile VACIS® Cargo, Vehicle and Contraband Inspection Unit to be Deployed at Latvian Points of Entry" [online], Jun. 17, 2004 [retrieved on Jul. 8, 2004], 2 pp., Retrieved from the Internet: http://www.saic.com/news/2004/jun/17.html.

"SAIC Canada Completes Acquisitio of Exploranium G.S. Limited" [online], Dec. 23, 2003 [retrieved on Jul. 8, 2004], 2 pp., Retrieved from the Internet: http://www.saic.com/news/2003/dec/23.html.

SAIC Awarded Strategic Port Automation Contract [online], Oct. 28, 2003 [retrieved on Jul. 8, 2004], 2 pp., Retrieved from the Internet: http://www.saic.com/news/2003/oct/28.html.

SAIC's Mobile VACIS to Inspect for Explosives and Contraband at U.S. Borders, U.S. Customs Awards Contract for 11 Mobile VACIS Units [online], Oct. 20, 1999 [retrieved on Jul. 8, 2004], 2 pp., Retrieved from the Internet: http://www.saic.com/news/oct99/news10-20-99.html.

SAIC's VACIS II to Search for Contraband at U.S. Borders, U.S. Customs Services Issues Contracts for 29 VACIS II's [online], Jul. 26, 1999 [retrieved on Jul. 8, 2004], 2 pp., Retrieved from the Internet: http://www.saic.com/news/jul99/news07-26-99.html.

"Rapiscan TVS™—Truck Validation System" [online], Copyright 1999-2002 [retrieved on Jul. 1, 2004], 3 pp., Retrieved from the Internet: http://www.rapiscan.com/4100.html.

"Mobile VACIS® Inspection System, Overview" [online], [retrieved on Jun. 3, 2004], 2 pp., Retrieved from the Internet: http://www.saic.com/products/security/mobile-vacis/index.html.

"Pallet VACIS® Inspection System, Overview" [online], [retrieved on Jun. 3, 2004], 2 pp., Retrieved from the Internet: http://www.saic.com/products/securitypallet-vacis/index..html.

"Portal VACIS® Inspection System, Overview" [online], [retrieved on Jun. 3, 2004], 2 pp., Retrieved from the Internet: http://www.saic.com/products/security/portal-vacis/index..html.

"Railroad VACIS® Inspection System, Overview" [online], [retrieved on Jun. 2, 2004], 2 pp., Retrieved from the Internet: http://www.saic.com/products/security/rr-vacis/index..html.

"Relocatable VACIS® Inspection System, Overview" [online], [retrieved on Jun. 2, 2004], 2 pp., Retrieved from the Internet: http://www.saic.com/products/security/relocatable-vacis/index..html.

"Rapiscan GaRDS™—Gamma Radiographic Detection System" [online], Copyright 1999-2002 [retrieved on Apr. 5, 2004], 3 pp., Retrieved from the Internet: http://www.rapiscan.com/4200main.html.

Richardson, Rex D., et al., "New Cargo Inspection and Transportation Technology Applications" [online], [retrieved on Feb. 18, 2004], pp. 83-90, Retrieved from the Internet: http://www.saic.com/products/security/relocatable-vacis.

O'Brien, Gregory, et al., "Non-Intrusive Container Inspection" [online], [retrieved on Feb. 18, 2004], pp. 1-3, Retrieved from the Internet: http://www.saic.com/products/security/relocatable-vacis.

Orphan, Victor J., et al., "VACIS™—A Safe, Reliable and Cost-Effective Cargo Inspection Technology" [online], [retrieved on Feb. 18, 2004], pp. 61-65, Retrieved from the Internet: http://www.saic.com/products/security/relocatable-vacis.

"DigestPlus Selector, My Product List" [online], [retrieved on Jun. 3, 2003], 1 p., Retrieved from the Internet: http://ecatalog.squared.com/fulldetail.cfm?partnumber=DTU223NRB.

"Thomas Compressors and Vacuum Pumps, Rietschle Thomas" [online], Copyright 2001 [retrieved on May 15, 2003], 1 p., Retrieved from the Internet: http://www.thomaspumps.com/products/security/relocatable-vacis.

"Thomas Compressors and Vacuum Pumps News, Kings of Custom, Rietschle Thomas, Sales & Distribution" [online], [retrieved on May 15, 2003], Retrieved from the Internet: http://www.dealer.thomaspumps.com/dealers/list_us_distribs.asp?request=5.

"Double Throw Safety Switches—Fusible and Not Fusible, 30 (Series T4), 200-600 A Types 82,000, 92,000 and 200 A DTU (Series E)" [online], [retrieved on Feb. 19, 2003], 1 p., Retrieved from the Internet: http://ecatalog.squared.com/catalog/html/sections/03/17203014.htm.

"U.S. Customs Service Inspectors Seize 2,362 Pounds of Marijuana at El Paso Port of Entry" [online], Mar. 8, 2002 [retrieved on May 22, 2002], 1 p., Retrieved from Internet: http://www.customs.gov/hot-new/pressrel/2002/0311-00.htm.

"U.S. Customs Service Inspectors Seize 234 Pounds of Cocaine at Presidio Port—High Tech Tools Help Pinpoint Drug Load" [online], Feb. 13, 2002 [retrieved on May 22, 2002], 1 p., Retrieved from Internet: http://www.customs.gov/hot-new/pressrel/2002/0215-03.htm.

"U.S. Customs Seizes $18 Million Load of Marijuana-Encased Cocaine From Commercial Bus in Eagle Pass" [online], Jul. 2, 2001 [retrieved on May 22, 2002], 1 p., Retrieved from the Internet: http://www.customs.gov/hot-new/pressrel/2001/0702-01.htm.

"Customs Seizes Marijuana from Two Commercial Trucks" [online], May 21, 2001 [retrieved on May 22, 2002], 1 p., Retrieved from the Internet: http://www.customs.gov/hot-new/pressrel/2001/0523-02.htm.

"U.S. Customs Service Inspectors Make Record Seizure at Santa Teresa Port—More Than 2-1/2 Tons of Marijuana Confiscated" [online], Feb. 4, 2002 [retrieved on May 22, 2002], 1 p., Retrieved from the Internet: http://www.customs.gov/hot-new/pressrel/2002/0207-01.htm.

"U.S. Customs Service Inspectors Locate 1,700 Pound Marijuana-Load—Seizure is One of Five Made at Nogales Tuesday" [online], Jan. 30, 2002 [retrieved on May 22, 2002], 1 p., Retrieved from the Internet: http://www.customs.gov/hot-new/pressrel/2002/0207-00.htm.

"U.S. Customs Inspectors in South Texas Seize $5.3 Million in Narcotics Over Veteran's Day Weekend" [online], Nov. 13, 2001 [retrieved on May 22, 2002], 1 p., Retrieved from the Internet: http://www.customs.gov/hot-new/pressrel/2001/1115-01.htm.

"U.S. Customs Inspectors Seize Over a Ton of Marijuana in Bus at Lincoln-Juarez Bridge, Two Arrested" [online], Nov. 6, 2001 [retrieved on May 22, 2002], 1 p., Retrieved from the Internet: http://www.customs.gov/hot-new/pressrel/2001/1106-00.htm.

"U.S. Customs Inspectors Seize 181 Pounds of Cocaine at Hidalgo/Pharr Port of Entry in Past Few Days" [online], Oct. 3, 2001 [retrieved on May 22, 2002], 2 p., Retrieved from the Internet: http://www.customs.gov/hot-new/pressre/2001/1004-01.htm.

"U.S. Customs Seizes Significant Marijuana Load in Bus at Roma Port of Entry" [online], Aug. 8, 2001 [retrieved on May 22, 2002], 1 p., Retrieved from the Internet: http://www.customs.gov/hot-new/pressrel/2001/0808-02.htm.

"Customs Inspectors in Naco and Nogales Stop Commercial Trucks Loaded With Dope—Seizures Net More Than 2,300 Pounds of Marijuana" [online], Jul. 20, 2001 [retrieved on May 22, 2002], 1 p., Retrieved from the Internet: http://www.customs.gov/hot-new/pressrel/2001/0720-02.htm.

"U.S. Customs Service Makes Record Drug Seizure at Santa Teresa Port of Entry" [online], Jul. 13, 2001 [retrieved on May 22, 2002], 1 p., Retrieved from the Internet: http://www.customs.gov/hot-new/pressrel/2001/0718-01.htm.

"U.S. Customs Inspectors Locate 1,296 Pound Marijuana Load in Commercial Truck at Nogales Port" [online], May 18, 2001 [retrieved on May 22, 2002], 1 p., Retrieved from the Internet: http://www.customs.gov/hot-new/pressrel/2001/0518-04.htm.

U.S. Customs Seizes Ton of Marijuana in Back-To-Back Seizures at World Trade Bridge Last Night—Inspectors Have Seized 4,407 Pounds at World Trade Bridge in Past Week [online], May 11, 2001 [retrieved on May 22, 2002], 1 p., Retrieved from the Internet: http://www.customs.gov/hot-new/pressrel/2001/0514-01.htm.

"U.S. Customs Inspectors Seize More Than Half-A-Million in Cash in Roma, One Arrested" [online], May 9, 2001 [retrieved on May 22, 2002], 1 p., Retrieved from the Internet: http://www.customs.gov/hot-new/pressrel/2001/0509-01.htm.

"U.S. Customs Inspectors Seize 3,089 Pounds of Marijuana at World Trade Bridge" [online], May 1, 2001 [retrieved on May 22, 2002], 1 p., Retrieved from the Internet: http://www.customs.gov/hot-new/pressrel/2001/0502-02.htm.

"U.S. Customs Seizes Over a Ton in Off-Road Trailer" [online], Mar. 13, 2001 [retrieved on May 22, 2002], 1 p., Retrieved from the Internet: http://www.customs.gov/hot-new/pressrel/2001/0315-00.htm.

U.S. Customs Seizes More Than 3,300 Pounds of Marijuana Hidden Inside Cargo Container [online], Mar. 9, 2001 [retrieved on May 22, 2002], 1 p., Retrieved from the Internet: http://www.customs.gov/hot-new/pressrel/2001/0313-00.htm.

"U.S. Customs Inspectors Seize $1.5 Million in Cocaine, Currency, Methamphetamine and Marijuana This Weekend at Port of Entry" [online], Feb. 12, 2001 [retrieved on May 22, 2002], 1 p., Retrieved from the Internet: http://www.customs.gov/hot-new/pressrel/2001/0213-02.htm.

"U.S. Customs Service Inspectors Seize 4,946 Pounds of Marijuana at El Paso/Ysleta Cargo Facility" [online], Jan. 30, 2001 [retrieved on May 22, 2002], 1 p., Retrieved from the Internet: http://www.customs.gov/hot-new/pressrel/2001/0130-02.htm.

"U.S. Customs Inspectors Seize 2,939 Pounds of Marijuana at World Trade Bridge This Weekend" [online], Jan. 29, 2001 [retrieved on May 22, 2002], 1 p., Retrieved from the Internet: http://www.customs.gov/hot-new/pressrel/2001/0130-01.htm.

"SAIC's Vacis II to Search for Contraband at U.S. Borders—U.S. Customs Services Issues Contracts for 29 VACIS Iis" [online], Jul. 30, 1999 [retrieved on Apr. 30, 2002], 1 p., Retrieved from the Internet: http://www.laprensasandiego.org/archive/july30/vacis.htm.

"Vehicle & Cargo Inspection System" [online], Jul. 30, 1999 [retrieved on Apr. 30, 2002], 1 p., Retrieved from the Internet: http://www.laprensasandiego.org/archieve/july30/vacis.htm.

Emery, Gail Repsher, "SAIC Sells Imaging Systems to Customs Service" [online], Mar. 20, 2001 [retrieved on Apr. 30, 2002], 1 p., Retrieved from the Internet: http://www.washingtontechnology.com/news/1_1/daily_news/16302-1.html.

U.S. Customs Service Orders Nine Railroad VACIS Units—SAIC's VACIS Technology to Be Used for Rail Car Inspections at Major U.S. Rail Border Locations [online], May 21, 2001 [retrieved on Apr. 30, 2002], 2 pp., Retrieved from the Internet: http://www.saic.com/news/may01/news05-21-01.html.

Double Throw Safety Switches, Fusible and Not Fusible, New—Series "F," Copyright 2002, 1 p.

Innovation Technology Summary Report (DOE/EM-0543), "Waste Crate and Container Imaging Using the Vehicle and Cargo Inspection System," Jul. 2000 (28 pp.).

SeaLevel Systems Incorporated, "Ultra 485™ User Manual," Copyright 1999, 24 pp.

Verbinski, Victor, et al., "Recent Developments in the VACIS Gamma Radiography Systems," *Part of the SPIE Conference on Enforcement and Security Technologies*, Boston, Massachusetts, SPIE vol. 3575, pp. 368-374, Nov. 1998.

Malotky, Lyle O., Pennella, John J., "Physics-Based Technologies for the Detection of Contraband," *SPIE—The International Society for Optical Engineering*, vol. 2936, pp. 112-113, Nov. 19-20, 1996.

Verbinski, Victor V., "Cargo Vehicle Inspection System," Sep. 28, 1995, *Proceedings—Counterdrug Law Enforcement: Applied Technology for Improved Operational Effectiveness International Technology Symposium*, Nashua, New Hampshire, Oct. 24-27, 1995, pp. 14-9-14-28.

"Imaging Gamma-Ray Contraband Detector for Empty Liquid Transport Containers," Quarterly Report, Work Carried Out Under: Contract No. DABT63-94-C-0039 (ONDCP), Prepared for: COTR: John Shaver, U.S. Army Electronic Proving Ground, Report Prepared by: Victor Verbinski, Science Applications International Corporation 15 pp., Nov. 21, 1991.

Award/Contract No. DABT63-94-C-0039, Issued by: Directorate of Contracting, Contractor: Science Applications International Corporation, Ship to: Office of National Drug Control Policy, Payment Will Be Made by: Defense Finance & Account Svc., Defense Accounting Office, 32 pp., Aug. 1994.

Verbinski, Victor V., "Contraband Detector for Tanker Trucks and Similar Vehicles," Jul. 1993, *Proceedings—Tactical Technologies and Wide Area Surveillance International Symposium*, Chicago, Illinois, Nov. 2-5, 1993, pp. 23-42.

"Proposal to Develop Imaging Gamma-Ray Contraband Detector for Empty Liquid Transport Containers," Technical Volume, Submitted to: Executive Office of the President, In Response to: ONDCP Broad Agency Announcement (BAA) 92-15 (Log No. 92-15-A222), Submitted by: Science Applications International Corporation, 54 pp., May 6, 1993.

"Contraband Detector for Tanker Trucks: Feasibility Study," Technical Proposal, Submitted to: Department of the Treasury, U.S. Customs Service, Contract No. TC 81-14, Submitted by: V. Verbinski, Science Applications International Corporation, 20 pp., Jul. 8, 1991.

Hasegawa, Bruce, H., et al., "A Prototype High-Purity Germanium Detector Systems with Fast Photon-Counting Circuitry for Medical Imaging," *Med. Phys.*, vol. 18, No. 5, pp. 900-909, Sep./Oct. 1991.

Docket for *Rapiscan Security Products, Inc. v. Science Applications International Corporation*, Docket 2:04-cv-02936-GPS-FMO (as of Jan. 10, 2005).

Orphan Victor J., et al., "VACIS™—A Safe, Reliable and Cost-Effective Cargo Inspection Technology," *Port Technology International*, pp. 61-65, Spring Edition 2002.

Emery, Gail Repsher, "SAIC Sells Imaging Systems to Customs Services" [online], *Washington Technology*, Mar. 20, 2001 [retrieved on Jan. 18, 2005], 1 p., Retrieved from the Internet: http://www.washingtontechnology.com/cgi-bin/ud/im.display.printable2client.id=wtdaily- . . . .

Richardson, Rex D., et al., "New Cargo Inspection and Transportation Technology Applications," *Port Technology International*, pp. 83-90, Winter Edition 2001.

Verbinski, Victor V., Orphan, Victor J., "Vehicle and Cargo Inspection System," SPIE, vol. 2867, pp. 235-238, Feb. 1997.

Boyd, Douglas P., Chapter 130, "Transmission Computed Tomography," *Future Technologies*, pp. 4357-4371 (1981).

Fetter, Steve, et al., "Detecting Nuclear Warheads," *Science & Global Security*, vol. 1, pp. 225-253, 1990.

Fetter, Steve, et al., "Appendix A—Fissile Materials and Weapon Design," *Science & Global Security*, vol. 1, pp. 255-263, 1990.

Fetter, Steve, et al., "Appendix B—Emission and Absorption of Radiation," *Science & Global Security*, vol. 1, pp. 265-285, 1990.

Mozley, Robert, "Appendix C—Particle Sources and Radiography," *Science & Global Security*, vol. 1, pp. 287-302, 1990.

Sukosd, Csaba, "Determination of Delayed Neutron Parameters and of Uranium Content of a Sample" [online], [retrieved on Sep. 1, 2005], 17 pp., Retrieved from the Internet: http://wwwreak.bme.hu/nti/Education/Wigner_Course/WignerManuals/Dudapest/DELAYED_NEUTRON.htm.

J.C. David, et al., "Mass and Charge Distributions From Photon-Induced Fission: Comparison With Experimental Data and Yields From Neutron Induced-Fission" [online], [retrieved on Sep. 1, 2005], 9 pp., Retrieved from the Internet: http://www-dapnia.cea.fr/Doc/Publications/Archives/dapnia-03-430.pdf.

Proposal No. 01-1769-71-2005-002, "VACIS-Z Upgrade for Photofission Detection of SNM," vols. I and II, Submitted to: Department of Homeland Security, Homeland Security Advanced Research Projects Agency (HSARPA), In Response to: Department of Homeland Security, Homeland Security Advanced Research Projects Agency (HSARPA), Part A, Technical Topic Area (TTA) 6—Detection Systems for Radiological and Nuclear Countermeasure (DSRNC) Broad Agency Announcement 04-02 (BAA 04-02), Submitted by: Science Applications International Corporation, 35 pp., Jul. 7, 2004.

"Non-Intrusive, High-Energy X-Ray Inspection System for Detection of WMD in Fully Laden Tanker Trucks and Cargo Containers," A Report Submitted in Response to: Request for Information by: DHS-Border and Transportation Security, United States Customs Service, Procurement Division, Classification Code: 58-Communications, Detection & Coherent Radiation Equipment, Solicitation Number: YY, Submitted to: Aaron Ford, Contracting Officer, United States Customs Service Procurement Division, Submitted by: Science Applications International Corporation, 7 pp., Nov. 3, 2003.

"VACIS-Z: A Dual-Energy X-Ray Imager for High-Z Materials Detection," A Phase III Proposal Submitted in Response to: BAA Announcement Number: DAAD05-03-T-0024, Submitted to: Combating Terrorism Technology Support Office, Technical Support Working Group, Submitted by: Science Applications International Corporation, 51 pp., Oct. 3, 2003.

"Vacis-Z: A Dual-Energy X-Ray Imager for High-Z Materials Detection," A Phase II White Paper Submitted in Response to: BAA Announcement No. DAAD05-03-T-0024, Submitted to: Combating Terrorism Technology Support Office, Technical Support Working Group, Submitted by: Science Applications International Corporation, 13 pp., Aug. 13, 2003.

BAA No. TSWG DAAD05-03-T-0024 DHS, Missing Area: 5.1 Chemical, Biological, Radiological and Nuclear Countermeasures (CBRNC), Requiring No. 1072/CB-1072-SAIC-1769-1, Proposal Title: "VACIS-Z: A Dual-Energy Betatron Imager for High Z Materials Detection," 1 p., Jun. 10, 2003.

White Paper for the Development of a "Low Cost, Relocatable, High Energy (7.5 MeV) X-Ray Cargo Imaging System for Detection of WMD," Submitted to: Department of Homeland Security, U.S. Bureau of Customs and Border Protection (CBP), Submitted by: Science Applications International Corporation, 6 pp., May 5, 2003.

J.L. Jones, et al., "Photonuclear Based Detection of Nuclear Smuggling in Cargo Containers," *17th International Conference on Application of Accelerators in Research and Industry*, Denton, Texas, 4 pp., Nov. 12-16, 2002.

C.E. Moss, et al., "Linear Accelerator-Based Active Interrogation for Detection of Highly Enriched Uranium," *17th International Conference on Application of Accelerators in Research and Industry*, Denton, Texas, 5 pp., Nov. 12-16, 2002.

S. Ogorodnikov and V. Petrunin, "Process of Interlaced Images in 4-10 MeV Dual Energy Customs System for Material Recognition," *Physical Review Special Topics—Accelerators and Beams*, vol. 5, pp. 104701-1-104701-11, 2002.

G.F. Knoll, "Radiation Detection and Measurement," John Wiley, Inc., New York, pp. 711-713, 9 pp., 2000.

M.F. Vorogushin, et al. "Experiments on Material Recognition for 8 MeV Customs Inspection System for Trucks and Large-Scale Containers," *XX International Linac Conference*, Monterey, California, 2000.

V.L. Novikov, et al., "Dual Energy Method of Material Recognition in High-Energy Introscopy System," *XVI International Workshop on Charged Particle Linear Accelerators*, Alushta, Crimea, Ukraine, 2 pp., Sep. 6-12, 1999.

V.L. Novikov, et al., "Dual Energy Method of Material Recognition in High Energy Introscopy Systems," *Proc. 16th International Workshop on Charged Particle Linear Accelerators*, Alushta, Crimea, Ukraine, 1999, appeared in ISSN 1562-6016, *Problems of Atomic Science and Technology*, vol. 4, p. 93, 1999.

"Handbook on Nuclear Activation Cross Sections," International Atomic Energy Agency, Technical Reports Series 156, p. 552, Vienna, 1974.

Jelley, "Cerenkov Radiation and Its Applications," Pergamon Press, New York, 1958.

Casey, M.E. and Nutt, R., "A Multicrystal Two-Dimensional BGO Detector System for Positron Emission Tomography," *Trans. Nucl. Sci.*, vol. 33, No. 1, pp. 460-463, 1986.

Roney, J.M. and Thompson, C.J., "Detector Identification with Four BGO Crystals on a Dual PMT," *Trans. Nucl. Sci.*, vol. NS-31, No. 5, pp. 1022-1027, Oct. 1984.

Derenzo, S.E., Budinger, T.F., Vuletich, T., "High Resolution Positron Emission Tomography Using Small Bismuth Germanate Crystals and Individual Photosensors," *Trans. Nucl. Sci.*, vol. NS-30, No. 1, pp. 665-670, Feb. 1983.

Derenzo, S.E., et al. "Imaging Properties of a Positron Tomograph with 280 BGO Crystals," *Trans. Nucl. Sci.*, vol. NS-28, No. 1, pp. 81-89, Feb. 1981.

"Smugglers Beware, Gamma Rays on Deck" [online], Sep. 11, 2003 [retrieved on Jan. 18, 2005], 2 pp. Retrieved from the Internet: http://nb.cbc.ca/regional/servlet/View?filename=nb_gam-maport2030911.

Clarke, Lavern, "Major Upgrade for Port Security-Contracts Signed for $1 Billion X-Ray Equipment" [online], *The Daily Gleaner*, Jul.

24, 2003 [retrieved on Jan. 18, 2005], 2 pp., Retrieved from the Internet: http://www.portjam.com/major_upgrade_for_port_security.html.

"Congressman Cardin Unveils Gamma Ray Scanner at Port of Baltimore" [online], Feb. 10, 2003 [retrieved on Jan. 18, 2005], Maryland Department of Transportation, 2 pp., Retrieved from the Internet: http://www.mdot.state.md.us/News/2003/February2003/MPA%20VACIS.

Barber, Mike, "Port Gets a New Tool to Fight Terrorism" [online], *Seattle Port Intelligencer*, Apr. 27, 2002 [retrieved on Jan. 18, 2005], 3 pp., Retrieved from the Internet: http://seattlepi.nwsource.com/printer2/index.asp?ploc=t&refer=http.seattlepi.nwsource.com..

International Search Report and Written Opinion for Application No. PCT/US07/06623, dated Feb. 7, 2008 (mailing date).

Verbinski, Victor V., and Orphan Victor J., "Vehicle and Cargo Container Inspection System for Drugs," *AIP Conference Proceedings*, vol. 475(1), pp. 682-686, Jun. 10, 1999.

"The Sentinel System Gamma Radiography System for Inspection of Railroad Cars, vol. 1: Technical and Management Proposal," SAIC Proposal No. 01-0488-71/0980-028 R1, Submitted to: Electronic Proving Ground, in Response to: BAA No. 98-001, Submitted by: Science Applications International Corporation, 41 pp., Aug. 1998 (REDACTED).

Supplementary European Search Report for Application No. 04821675.8, dated Apr. 10, 2007.

White Paper, "Automated, High-Speed Non-Intrusive Inspection of Empty Cargo Containers," 5 pp., Jul. 5, 2002.

International Search Report and Written Opinion for Application No. PCT/US04/31725, dated Sep. 30, 2005 (mailing date).

"Containing Terror—Electronic Seals and Tracking Efforts Boost Cargo Security," *Technology Review*, pp. 24-25, Sep. 2003.

Levin, et al., "A Monte Carlo Correction for Compton Scattering Effects in 3D PET Brain Imaging," *IEEE*, pp. 1502-1506, 1995.

\* cited by examiner

SYSTEM AND METHOD FOR THREE-DIMENSIONAL IMAGING USING SCATTERING FROM ANNIHILATION COINCIDENCE PHOTONS

CROSS REFERENCE TO RELATED APPLICATIONS

This application is a continuation of and claims priority to U.S. patent application Ser. No. 12/939,449, filed Nov. 4, 2010, entitled "System and Method For Three-Dimensional Imaging Using Scattering From Annihilation Coincidence Photons," which claims priority to U.S. Provisional Patent Application Ser. No. 61/257,874, filed on Nov. 4, 2009, and titled "Three-Dimensional Imaging System and Technique Using Measured Sideways Scattering From Annihilation Coincidence Photons," both of which are incorporated herein by reference.

BACKGROUND OF THE INVENTION

1. Field of the Invention

The present invention relates generally to the field of imaging using photons and more specifically to imaging using coincidence photons generated from electron-positron annihilation.

2. Description of the Related Art

In positron emission tomography ("PET") imaging, a radioisotope source emits positrons that combine with electrons and annihilate, each annihilation producing a pair of oppositely directed 511 keV photons. The volume being imaged is placed between a pair of position-sensitive gamma photon detector arrays. The coincident detection of a pair of photons on the two detector arrays signals that an annihilation event has been detected. The position of the annihilation event can be deduced as having occurred at some point along a straight line joining the two points of detection. Time-of-flight information can be used to somewhat further localize the position of the annihilation to some section along this line, limited by the timing resolution of the photon detection systems. The typical application is to use these projected points of annihilation to build up a three-dimensional map of annihilation density and measure the uptake of short-lived radioisotopes within human patients for diagnostic purposes.

PET imaging systems are designed to localize the position of the radioisotope materials. The invention described in the Detailed Description of the Exemplary Embodiments that follows modifies the PET imaging process so that annihilation coincidence photons can be used for imaging of other targets.

A landmine detection system has been described by J. R. Tickner, M. P. Currie, and G. J. Roach in "Feasibility study for a low-cost 3D gamma-ray camera," Applied Radiation and Isotopes 61 (2004) 67-71. This system uses a positron annihilation source to create probe photons with known directions and time. Instead of the use of a return-scatter directional detection technique, time-of-flight is used to establish some three-dimensional information as to the scattering locations. However, the prior art in time-of-flight scattering measurements using annihilation coincidence photons lacks accurate resolution in the third dimension through limitations in the state-of-the-art in radiation detector timing resolution.

So-called "flying-spot" backscatter imagers utilize a rotating collimator and a bremsstrahlung x-ray source to generate a rastered x-ray beam. When this beam is swept over a target, either by moving the source or the target through the rastering beam, a two-dimensional image is formed by detection of photons backscattered from the target. The flying-spot systems utilizing a bremsstrahlung x-ray source do not image in the third dimension. Also, because the outgoing probe photons from the x-ray source are not mono-energetic, it is not possible to use energy of the return scattered photons to discriminate single—from multiple-scatter events. Furthermore, bremsstrahlung x-ray sources produce many x-ray photons at lower energy that have significantly inferior penetration capability than higher-energy mono-energetic photons, and consequently produce images with less penetration and reduced contrast for a given fixed radiation dose to the target than a mono-energetic source will yield. X-ray equipment also tends to be complex and requires significant maintenance.

SUMMARY OF THE INVENTION

Summary of the Problem

There is a need for an apparatus and a method that provides more accurate imaging with scattered photons. This need includes the need for more accurate three-dimensional imaging through imaging of the return scattered photons from a single side of a target. Single-sided imaging tools have a distinct advantage over imaging systems that require access to both sides of the target.

Summary of the Solution

The invention improves image quality, contrast and penetration for a given radiation dose to the target. It does this by reducing uncertainty in the measurement process, extracting more information from each scattered photon detected from the target. Each scattered photon received can be associated, by timing coincidence, with an outgoing probe photon. Furthermore, the outgoing probe photon's trajectory has been determined, through measurement of the coincident photon in the annihilation pair, so the position at which the scattering took place is well localized. This reduces the build up of image variance (noise) in constructing the three-dimensional image.

In a first exemplary embodiment, a method for creating an image of a target is described. The method includes arranging a radioisotope source that emits positrons that collide with electrons producing a pair of photons. The first of the two photons collides with a gamma detector which measures a first trajectory and a first time associated with the first photon. An imaging software module uses the measured first trajectory and first time associated with the first photon to calculate a second trajectory and a second time associated with the second photon. The second photon collides with the target and produces a scattered photon. An imaging detector detects the scattered photon measuring a scattered trajectory and a scattered time associated with the scattered trajectory. The imaging software module can calculate a position for the target using the first trajectory, the first time, the second trajectory and the second time.

In a second exemplary embodiment, a system for creating an image of a target is described. The system comprises a radioisotope source that generates a positron that collides with an electron producing a pair of photons. The system further comprises a photon tagger that detects a first photon from the photon pair and measures a first trajectory and a first time associated with the first photon. An imaging software module uses the first trajectory and the first time to calculate a second trajectory and a second time associated with the second photon. The second photon collides with the target and produces a scattered photon. The system also comprises a detector measuring a scattered trajectory and a scattered time associated with the scattered photon. The imaging software module can use the first trajectory, the first time, the second trajectory and the second time in creating an image of the target.

In a third exemplary embodiment, a computer program product for creating an image of the target comprises a series of instructions to be executed by a computer. The instructions comprise instructions for receiving a first trajectory and a first time from a gamma detector, the first trajectory and the first time associated with a first photon of a photon pair created by positron-electron annihilation. The instructions further comprising instructions for calculating a second trajectory and a second time associated with a second photon. The instructions also comprising instructions for receiving a scattered trajectory and a scattered time from an imaging detector, the scattered trajectory and the scattered time associated with a scattered photon created by a collision between the second photon and the target. The instructions further comprising instructions for using the second trajectory, the second time, the scattered trajectory and the scattered time for creating an image of the target.

These and other embodiments are described in the detailed description that follows and the associated drawings.

BRIEF DESCRIPTION OF THE FIGURES

The preferred embodiments of the present invention are illustrated by way of example and are not limited to the following figures.

DETAILED DESCRIPTION OF THE EXEMPLARY EMBODIMENTS

Figure 1:
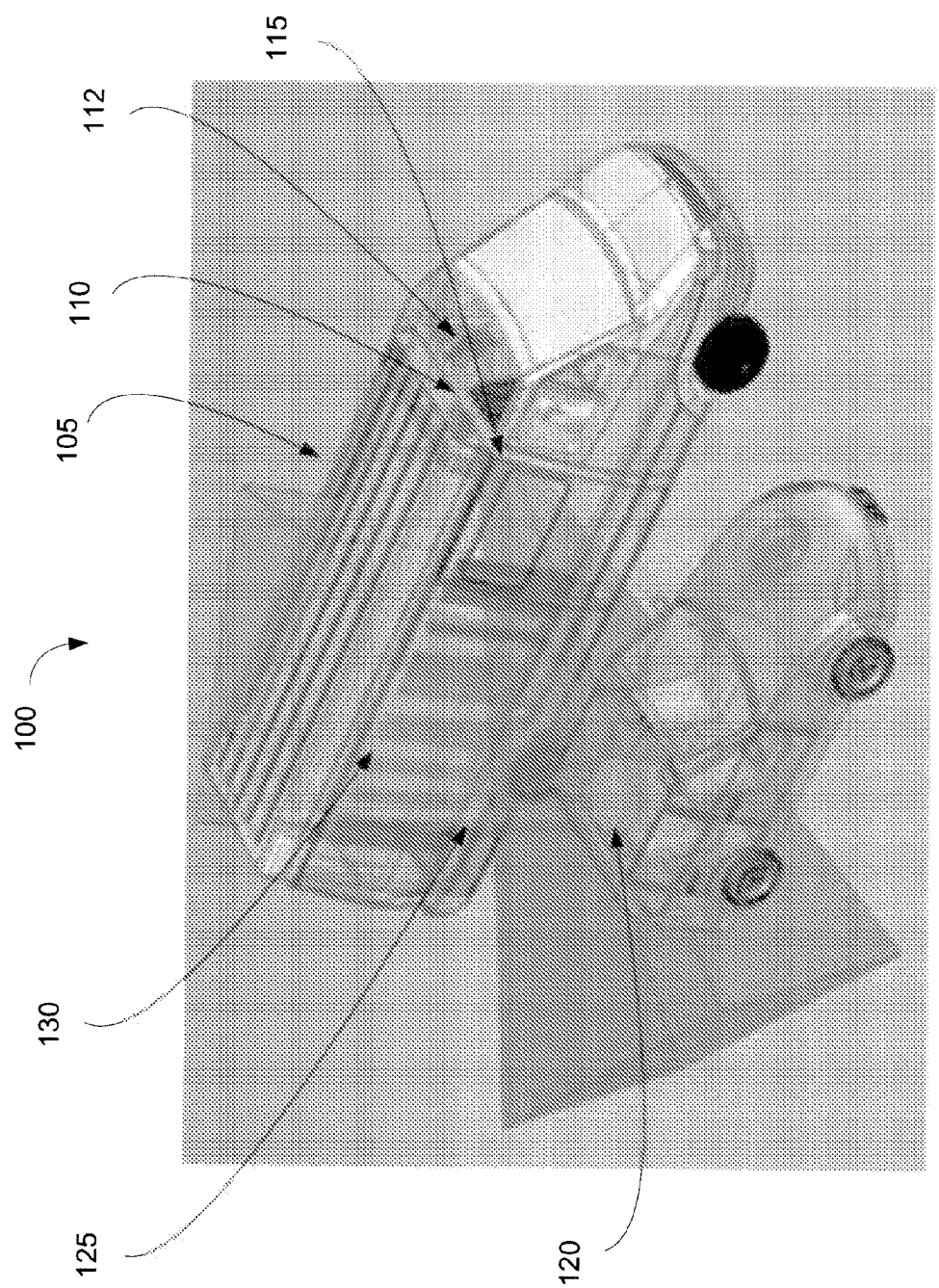
FIG. 1 illustrates the components of a backscatter imaging system in accordance with an exemplary embodiment of the present invention.

The invention includes a method using electron-positron annihilation coincidence photons to form a radiographic image of a volume directly in three dimensions without the need for multiple source and detector viewpoints to form said image. The reconstructed image contains three-dimensional information on radiographic density and also allows some estimates of the atomic number of the materials imaged in the volume. Such a system can be used to form three-dimensional images of a volume when access to only one side of the volume is available.

The present invention turns the PET imaging process around. The system uses a compact radioisotope source in a known location, and the detection of one of the coincident photons in the pair to determine the trajectory and emission time of the other photon in the pair. This mechanism is used to generate a source of photons that have been "tagged" in their direction and time.

The invention described also relies on a return-scatter directional detector to measure the arrival time and provide some directional information on the return scattered photons detected from the region being imaged. While there are a number of techniques for doing such detection, coded-aperture imagers are the most likely candidate in the system we describe.

The current state-of-the-art in radiation detector timing resolutions limits the ability to solely use time-of-flight to determine the length along the outgoing probe photon's trajectory at which the scattering occurred. The invention described recovers resolution in this third dimension by imaging the return scattered photons with a directionally-sensitive detector positioned on the same side (relative to the target) as the outgoing probe photon's direction. Even if the directionally-sensitive return scatter detector is probabilistic rather than deterministic in its sensitivity to return photon direction (in the manner of a coded-aperture imager), the combination of fine directional sensitivity in the directional detector, and deterministic limiting of possible scattering positions in the field-of-view (through outgoing photon trajectory measurement and time-of-flight information) allows the reconstruction in fine detail while reducing the variance build up the image formed.

The exemplary embodiments of the invention further reduce variance in the image using some or all of the following data: time-of-flight information, the measured outgoing photon trajectory, the deterministically measured position of detection of the scattered photon, the known energy of the outgoing probe photon, the measured energy of the return scattered photon, and the well established energy-versus-scattering-angle relationship in Compton scattering to discriminate scattered photons that have returned via a single—rather than a multiple—scattering interaction. This capability allows further improvement in contrast by only directly placing single-scattered photons in the reconstructed image whose scattering position can be established through intersection between the outgoing photon's measured trajectory and the direction measured of the return scattered photon.

Describing generally an exemplary embodiment of the invention, positrons of sufficiently low energy are captured within a small source-generation region, where they combine with electrons in atoms in the region and annihilate. A compact positron-emitting radioisotope source either of sufficient thickness itself to stop some proportion of emitted positrons, or contained within a source holder of sufficient thickness to do so, is one method for generating such annihilation events in a small region. However, the positrons may be generated elsewhere and impinged on the small source generation region where the recombination occurs.

Each annihilation releases a pair of photons, each of approximately 511 keV, in coincident pairs that travel in essentially opposite directions. By detecting the direction and time of emission of one photon in the coincident pair, and through the known location of the small recombination region where the annihilation event is known to have taken place, the trajectory and emission time of the other photon (the outgoing probe photon) in the coincident pair can be deduced. In the context of this document, these outgoing probe photons are referred to as "tagged".

A target volume to be imaged is exposed to tagged photons. The region being irradiated can be adjusted through collimation to include whatever region of interest is convenient. The tagged photons traversing the volume interact with matter in the volume. Many of the interactions will generate secondary photons that scatter from atoms in the volume at some angle to the tagged photon's incident trajectory.

A detector system situated at some angle to the outgoing tagged photon's trajectory is sensitive to the direction, time and optionally the energy of any return scattered photons that enter the detection region. This sub-system will be referred to in this document as the "return-scatter directional detector". Through time-coincidence between the detection of any scattered photons and the outgoing tagged-photon's deduced time of traversing the volume being imaged, some fraction of the return photon or photons detected can be associated with the outgoing tagged photon that generated it.

High-energy photons traversing a material have a non-zero probability of traveling some finite distance through the material without experiencing any interaction at all. As such, the photon has traveled through the material unchanged to this point. Some proportion of the tagged photons used to irradiate the volume being inspected will penetrate to some depth within the materials being imaged within the volume, undergo a single scattering interaction, then exit the volume being imaged without undergoing any further interactions. These are referred to in this document as "single-scatter events". Because photons in this energy range travel in essentially straight lines between interactions, and we have directly determined the trajectory of the outgoing tagged photon, we deterministically know that any single-scattered photons detected have returned from some point along the outgoing tagged-photon's trajectory. Furthermore, by imaging the return scattered photon's return direction at some angle to the side of the outgoing tagged-photon's trajectory, the scattering locations of single-scattered photons can be reconstructed in three-dimensions by projecting the imaged scattered photon's direction back onto the outgoing tagged photon's trajectory. Techniques for discriminating single—from multiple-scatter events will be described in the description of the exemplary embodiments that follows.

The return-scatter detector may image the return scattered photon direction in one or two dimensions, and in both cases yield sufficient information to reconstruct a three-dimensional map of scattering locations. Some types of return-scatter detectors may deterministically locate the return scatter direction in two dimensions, such as through a pinhole-aperture camera, or deterministically in one dimension through a slit-aperture camera. Other types only probabilistically project possible return scatter directions. Examples of such imaging devices are Compton cameras or one- or two-dimensional coded aperture arrays. A significant point with the present invention is that the outgoing photon's trajectory is known directly in two dimensions through the photon-tagging process described above, and that the side imaging through the return-scatter directional detector allows projection back to the measured outgoing trajectory to determine the third dimension of the scattering location.

The principle photon scattering mechanisms of utility in this invention, and by far the dominant interaction mechanism for photons in the energy range of 511 keV are Compton scattering and photoelectric absorption. These two mechanisms have different characteristics, both of utility to this invention.

Compton scattering will produce secondary scattered photons that exit at some angle from the trajectory of the incident photon being scattered. For Compton scattering from a free and stationary electron, the energy of the scattered photon from a single interaction is completely predictable from the energy of the incident photon and the angle of scattering. To a good approximation, the energy and momentum of atomic electrons in all but the lowest orbitals of the highest-atomic-number atoms are relatively insignificant in comparison to the energy and momentum transfers involved in Compton scattering of a 511 keV photon. As such, these energies and momenta can be ignored, and to a good approximation the energy of single-scattered photons for most materials in the volume being imaged can be predicted from the angle of scattering. Photons whose energy, as measured in the return-scatter directional detector, do not match the energy predicted for single-scatter events can be rejected from being included in the tally of single-scatter events. This technique will improve the contrast in the reconstructed image, by rejecting multiple scatter events whose scattering position cannot be directly determined in three dimensions.

A complicating factor is that some return-scatter directional detectors, for example coded-aperture arrays, do not deterministically measure the return angle of every photon detected. Instead, such detectors probabilistically assign the scattering location to multiple positions in the field of view. As such, a one-to-one prediction of the single-scatter energies of individual return-scattered photons detected cannot be made as the assumed single-scatter angle cannot be calculated deterministically. To overcome this problem, the secondary mechanism of measured time-of-flight between emission of the outgoing tagged photon and detection of the return scattered photon, in conjunction with the known point of emission of the outgoing tagged photon; its deterministically measured outgoing trajectory; and the deterministically measured point of detection of the return scattered photons; is employed through simple trigonometry to estimate the angle of an assumed single-scatter event. From this, an estimate of the expected single-scatter-return-photon energy can be made and a single-scatter energy window applied to return-scattered photons to preferentially select single-scattered photons over multiple-scattered photons. In more general terms, all measured information available, such as outgoing tagged-photon trajectory, time-of-flight-single-scatter-energy prediction, measured return-photon energy and any probabilistic return-angle information from the return-scatter angular detector are combined to optimally project probability of scattering location out to the three-dimensional field of view in the volume being inspected.

In low to moderate atomic number materials, in the energy range of the outgoing tagged photon and single-scatter return photon energies, Compton scattering is by far the dominant photon interaction mechanism. The photon attenuation mechanism in Compton scattering produces secondary scattered photons that can be detected. As such, we can estimate the attenuation of photons traversing through material within a volume, by measuring the number of secondary photons scattering sideways out of the volume. Once an optimal estimate of return scattering locations has been reconstructed within the three-dimensional volume being inspected, a secondary iterative process can be invoked in which the estimates of the radiographic density along the path through which primary tagged photons have entered into and traversed through the volume being imaged, and along the paths through which scattered photons have returned from the volume to the return-scatter directional detector, is used to compensate for attenuation along both paths. The radiographic density of materials in the foreground is directly estimated from the flux of single-scattered photons detected from these materials. These estimates are then used to progressively estimate the attenuation of the tagged-photon illumination and the return-scatter yields from materials behind the foreground materials. From this, a three-dimensional maximum-likelihood estimate of the three-dimensional radiographic density throughout the volume being imaged can be established, at least to a depth where sufficient photon statistics are available, and cumulative errors in the radiographic density have not caused divergence of the density estimates.

In higher-atomic-number elements in materials within the volume, the proportion of photo-electric absorption events to Compton scattering will be higher. In a photoelectric absorption event, all of the incident photon energy is transferred to an atomic electron within the volume, and no secondary scattered photon is produced (at least in many cases not of an energy adequate to exit the volume and make it to the return-scatter detector). This may frustrate some of the attempts to iteratively estimate radiographic density at depth within the volume. However, it is also possible that sufficient information will be available to discriminate higher-atomic-number materials throughout the volume by detecting components sections within the volume in which the attenuation of both the incident tagged photons and exiting scattered photons is higher in proportion to the amount of scatter being measured from such component sections. This would rely on gauging scatter from objects behind the object in question. Imaging from several different tagged-photon source and return-scatter detector positions could help with separating out such effects, as could knowledge of some of the elemental composition of materials in the field of view, such as assumed materials in body paneling of automobiles being imaged.

As mentioned previously, the photoelectric absorption mechanism knocks an electron from an atom. The ionized atom is then left with a vacancy in one of its atomic-state orbitals. The subsequent re-capture of an electron, or de-excitation of the ionized atom will often lead to the emission of either an optical or an x-ray photon. In the case of the highest-atomic-number materials the de-excitations from ionizations of deep core atomic electrons can produce x-ray photons in the order of 100 keV. In such cases, in certain configurations of materials within the volume, it may be possible to directly detect these x-rays, and to image and directly identify the location and elemental composition of such high-atomic-number elements within the volume.

Turning to the drawings, in which like numerals indicate like elements throughout the figures, exemplary embodiments of the invention are described in detail. Referring now to FIG. 1, an exemplary embodiment of a system 100 using annihilation coincidence photons for three-dimensional imaging is illustrated. As shown in FIG. 1, the imaging system 100 can be placed in a vehicle 105 for mobility. The imaging system 100 comprises a positron source 110, a photon tagger 112, and a return-scatter directional detector 130. In the exemplary embodiment 100, the positron source 110 comprises a radioisotope that emits positrons, such as a pellet of radioactive Na-22. The emitted positrons combine with electrons either within the positron source 110 or within a holder surrounding the positron source. When a positron and electron combine, they annihilate each other forming two photons that travel in essentially opposite directions. In the preferred embodiment of system 100, a holder surrounding the positron source 110 comprises two diametrically placed windows which are opened to release the two photons.

The photon tagger 112 positioned outside one of the windows of the holder detects the direction and time of emission for one photon in the coincident pair. For example, the photon tagger 112 can be a high-speed position-sensitive gamma photon detector widely used in nuclear medicine. The photon tagger 112 can measure in two dimensions the photon's point of intersection with the surface of the photon tagger 112. Using the recombination location where the annihilation took place and the detected direction and time of emission measured by the photon tagger 112, a computing device coupled to the photon tagger 112 can calculate the trajectory and emission time of the outgoing probe photon.

A collimator can be used to direct a beam of outgoing probe photons 115 towards a target volume 120 that is to be imaged. The outgoing probe photons 115 are able to penetrate the target volume 120, however, the dose of photons is small enough that it does not present health hazards for nearby people. A certain volume of backscatter photons 125 are directed from the target volume 120 to the return-scatter directional detector 130. As described above, a variety of different detectors can be used as the return-scatter direction detector 130. Detecting the backscatter photons 125 allows the exemplary system 100 to create an image of the volume elements ("voxels") within the target 120. In the preferred embodiment, the system 100 can create a three-dimensional image of the target 120 with a resolution of 1.5 cm.

Target objects with densities comparable to or less than water can be imaged to a depth of several centimeters. Target objects with higher densities do not permit significant penetration of the outgoing probe photons 115. Focal length adjustments to the outgoing probe photons 115 and the return-scatter direction detector 130 in conjunction with increased acquisition time can yield enhanced imaging resolution for the penetrable region of higher density objects.

The imaging method with exemplary system 100 relies on photons that return through only one scatter, as opposed to multiple scattering interactions. Each photon in the backscatter photons 125 is measured with respect to its energy, the time each reaches detector 130, and the position at which it strikes the detector 130. Using this information measured at the return-scatter direction detector 130, coupled with the information measure by the photon tagger 112 and the well-known Compton energy-versus-scattering-angle relationship, allows the exemplary system 100 to identify and discard photons from multiple-scatter or background events. By limiting the data to single-scatter events, the system 100 can improve image quality and contrast as compared to the broad energy spread in photons used in x-ray based backscatter imagers.

Figure 2:
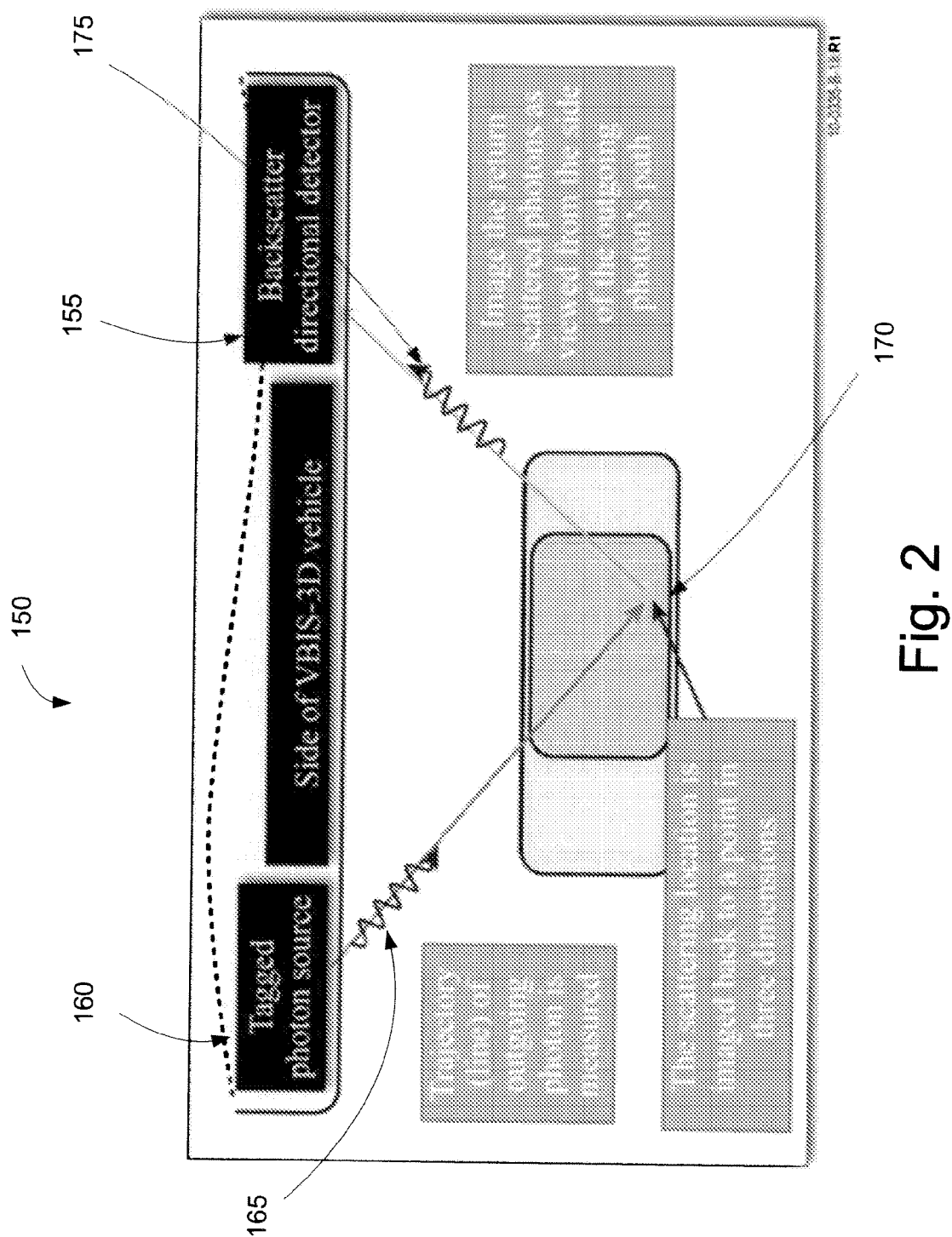
FIG. 2 illustrates the components of a backscatter imaging system in accordance with an exemplary embodiment of the present invention.

Referring to FIG. 2, a top-view schematic illustration is provided for an exemplary embodiment of the present invention. Exemplary imaging system 150 illustrated in FIG. 2 comprises tagged photon source 160 and backscatter directional detector 155. As described previously, the direction and time of the outgoing probe photon 165 are determined at the tagged photon source 160. The outgoing probe photon 165 collides with target volume 170 and backscattered photon 175 is detected by the backscatter directional detector 155.

An imaging software module installed on a computing device receives the data collected at the tagged photon source 160 and the data collected at the backscatter directional detector 155 and reconstructs a one-dimensional image along the known tagged track of the outgoing probe photon 165. If the imaging software module determines, based on the collected energy and time data, that the backscattered photon 175 was scattered more than once, the data for that photon is discarded from use in constructing the image of the target. Data for single-scatter photons is collected over a period of time, such as three minutes, and the imaging software module can build a three-dimensional image of the target.

Figure 3:
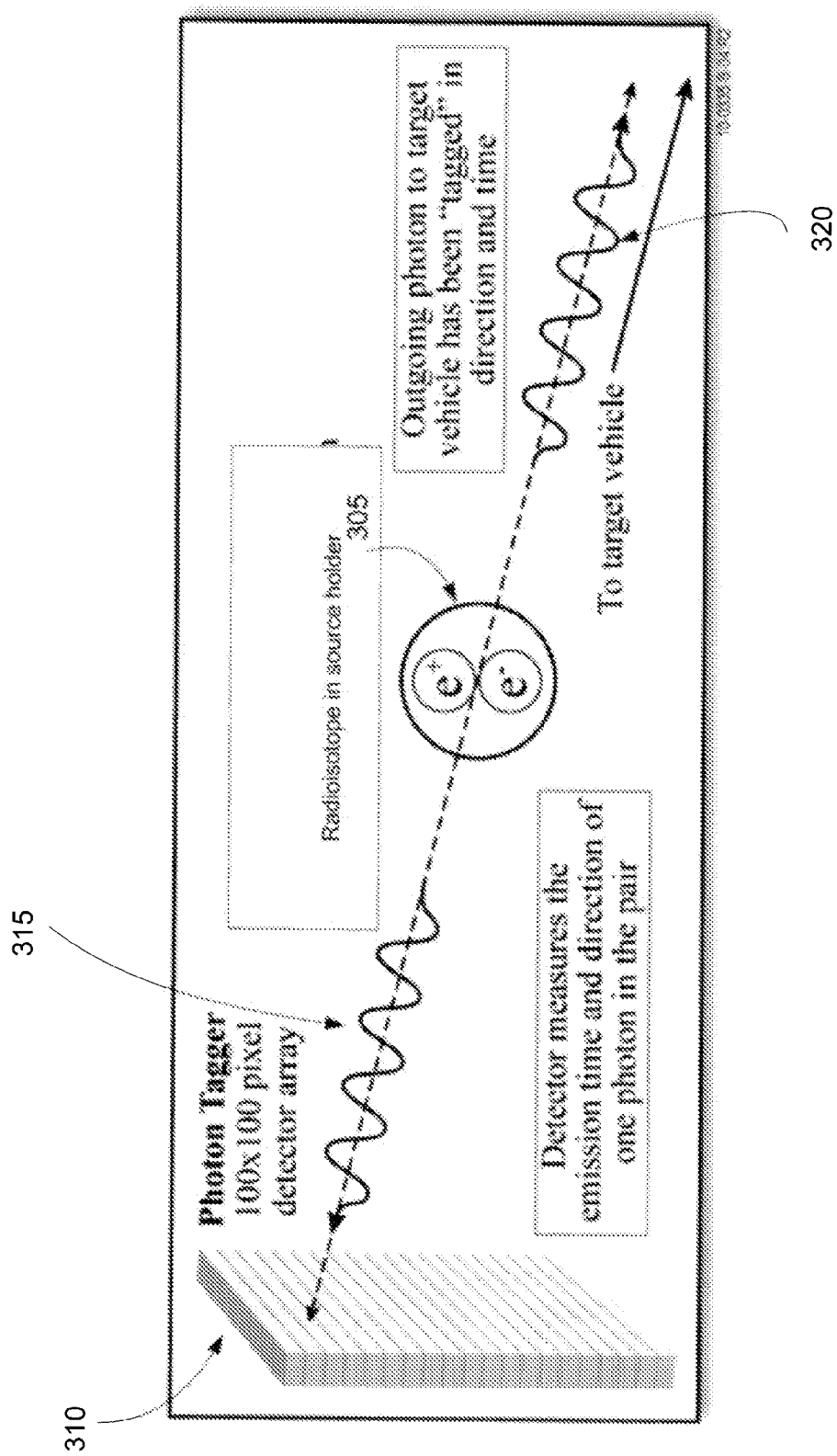
FIG. 3 illustrates the use of a photon tagger in accordance with an exemplary embodiment of the present invention.

Referring to FIG. 3, an exemplary method for tagging an outgoing probe photon is illustrated. FIG. 3 shows a photon tagger 305, a radioisotope source 310, a first photon 315 and an outgoing probe photon 320. As shown in FIG. 3, the position of the radioisotope source 310 and, therefore, the point at which the photons are generated from a positron-electron collision are both known. The photon tagger 305, such as those used in PET medical imaging, intercepts the first photon 315 and measures both the trajectory and emission time of the intercepted first photon 315. The data the photon tagger 305 collects from the intercepted first photon 315 permits an imaging software module installed on a computer to determine the trajectory of the outgoing probe photon 320.

An exemplary photon tagger, such as photon tagger 305, typically comprises a segmented scintillator optically coupled to a number of photomultiplier tubes (PMT) or avalanche photodiodes (APD). The scintillator converts each photon received into a pulse of optical photons. Because of the high count rates involved, a fast scintillator, such as lutetium oxyorthosilicate (LSO) is preferred. The PMTs or APDs detect the optical photons and generate an amplified electrical pulse.

A standard technique for a photon tagger is to place multiple PMTs on the back of the scintillator. The light pulses are generated at the point of initial scattering of the first photon in the scintillator and at possible subsequent secondary scattering sites close to this initial interaction point. By measuring the relative amount of light shared between the PMTs, the point the photon entered the detector can be established.

With respect to the positron source, a radioisotope with an activity of approximately 20 millicurie should be sufficient for the imaging. One example of a commercially available holder that can be used for containing the source is an Ohmart-Vega rotary shutter source holder such as the SHLD-1.

Figure 4:
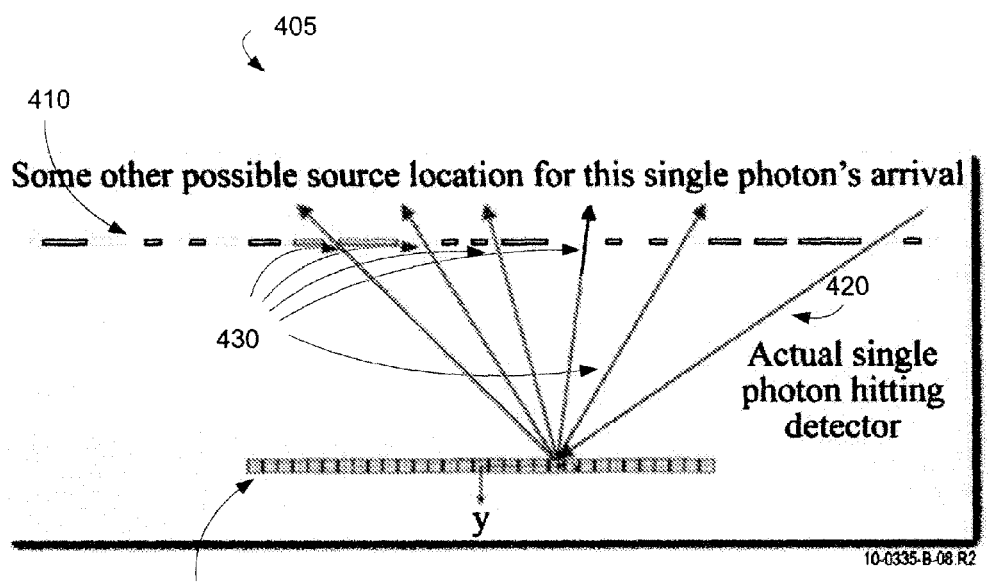
FIG. 4 illustrates a coded aperture mask and detector array in accordance with an exemplary embodiment of the present invention.

Referring to FIG. 4, a one-dimensional coded aperture mask pattern and detector array in accordance with an exemplary embodiment of the invention is illustrated. The coded aperture detector 405 comprises a patterned mask 410 positioned in front of a detector array 415. The patterned mask 410 is typically 50% open with the mask being thick enough to stop the backscatter photons except for those backscatter photons that pass through the openings in the patterned mask 410.

Arrow 420 in exemplary FIG. 4 points to a single hit of a backscatter photon on a single detector in detector array 415. Arrows 430 illustrate some of the many other possible directions from which the photon could have arrived at the detector. Absent other information, it would be difficult to determine from which direction a single photon arrived. However, after a certain number of photons are detected by detector 405, the points in the field of view consistent with the arrivals quickly narrows down to a single point.

Figure 5:
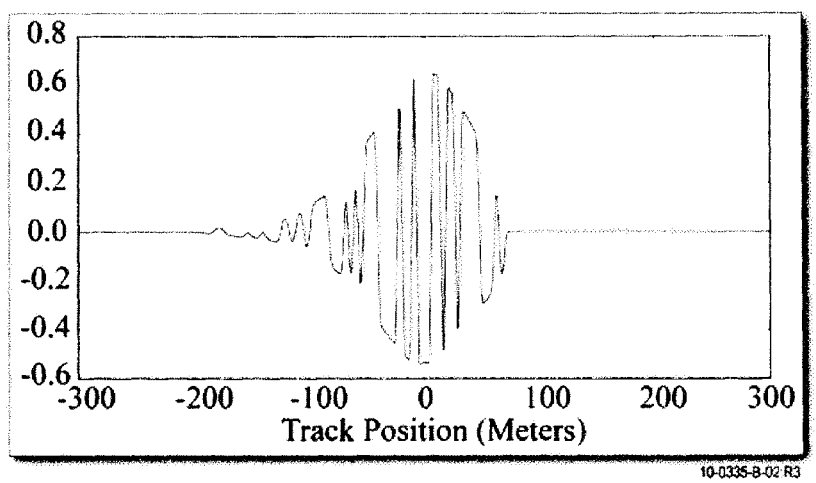
FIG. 5 illustrates a reconstruction kernel in accordance with an exemplary embodiment of the present invention.

A reconstruction kernel, such as the example illustrated in FIG. 5, can track the detected photons arriving at the various detectors in the detector array 415. The reconstruction kernels project back to the outside world a probability map of positions from which each photon could have arrived. Each detector in the detector array 415 typically has a different reconstruction kernel. The reconstruction kernel should incorporate all known a-priori information about the relative probabilities of arrival from all the possible source locations for each detected photon.

The exemplary imaging system, such as those described in connection with FIGS. 1 and 2, has significant a-priori information about the photons intercepted at the coded aperture detector 405. Because the trajectory of the outgoing probe photon is known from the measurements at the photon tagger, the only possible return scattering locations are on the measured line of the outgoing probe photon's track. Additionally, because the imaging system measures the outgoing time and return time of each photon, the track of the outgoing probe photon can be limited to a certain range based on the measured time data.

The reconstruction kernel illustrated in FIG. 5 is a calculated optimal reconstruction kernel for a photon hit at the coded aperture detector. The reconstruction kernel shown in FIG. 5 was derived to locate a source at an assumed distance of 75 meters from the imager. The positive sections of the kernel add probability to the photon track sections visible through the mask, whereas the negative sections subtract probability for the photon track sections blocked by the mask.

A desirable characteristic in a coded aperture mask is the so-called "ideal response." For each hit on a detector, a probability can be dispatched to the field of view that the photon arrived through any of the open sections. Each hit at the detector dispatches probability to many places from which the photon did not arrive. While this is unavoidable, a mask pattern can be selected that, on average, dispatches the maximum probability to the correct point and a flat uniform probability to other points in range of the kernel. In fact, coded aperture masks with an autocorrelation function that is a single central peak with flat trails exhibit this ideal response.

Figure 6:
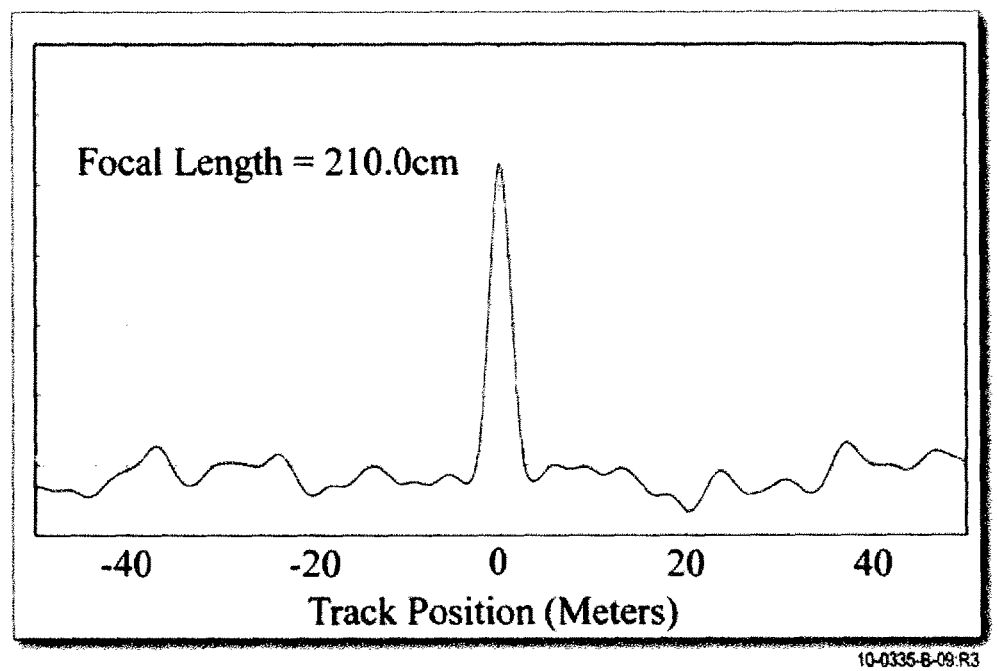
FIG. 6 illustrates a calculated point-spread function for a coded aperture detector in accordance with an exemplary embodiment of the invention.

FIG. 6 illustrates a calculated point-spread-response for an imager with a focal length of 210 cm from mask to detector. The full-width at half maximum corresponds to 40-milliradian resolution at 75 meters. Applying a similar imager at 3 meters for the embodiment described in FIGS. 1 and 2, the imager would have a resolving power of 12 cm for the 210 cm mask-to-detector focal length.

Multiple counts on multiple detectors are dispatched through the reconstruction kernel to build an image with a sharpness given by the system's point spread function. However, the kernel adds variance over a wider range. The process can be understood by imagining photons randomly entering from a single point source in the field of view. The photons will come through various open sections of the mask and hit various detectors; each hit will dispatch probability out to the field of view. The correct point in the field of view will always be receiving positive contributions from the various reconstruction kernels from the various detectors hit. Incorrect points nearby will sometimes receive positive contributions and sometimes receive negative contributions. The mean of these contributions for incorrect points will tend to zero; however, the variance from these contributions adds up over the entire non-zero width of the kernels. Fortunately, in our application, a-priori tagged-photon-track and range-gating information limit these kernel widths to a small volume. This noise variance only spreads out along the direction imaged by the coded aperture. The photon tagger for each photon measures the other two directions deterministically, so there is no variance spread in these other two directions.

Figure 7:
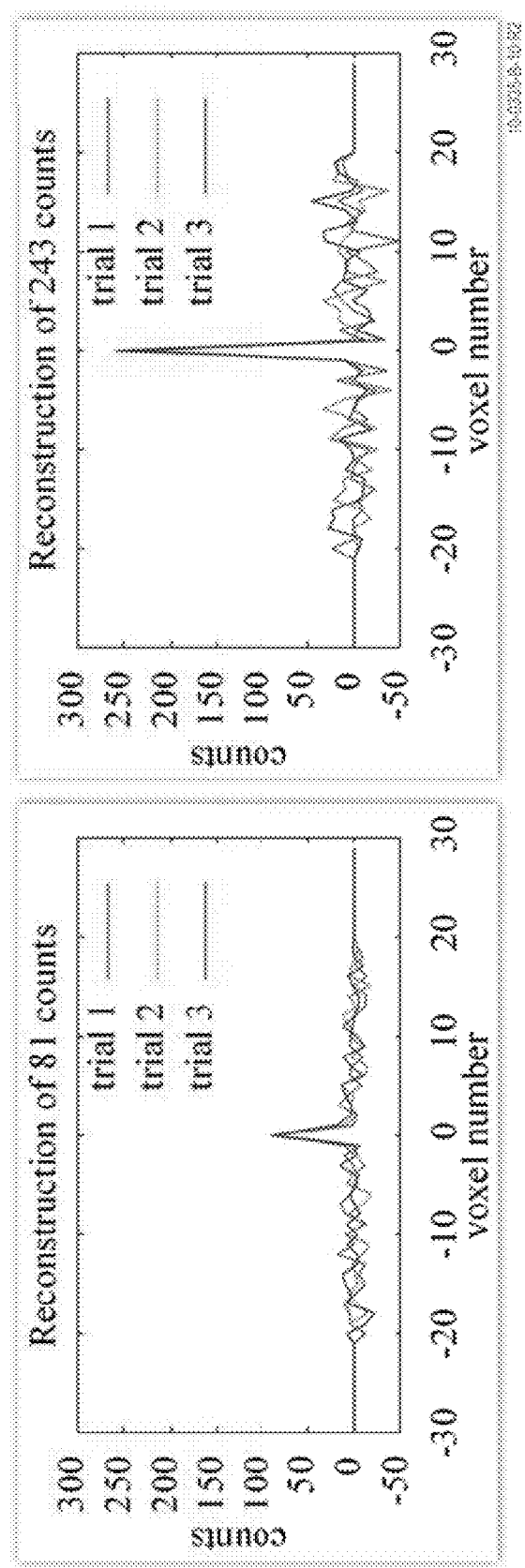
FIG. 7 illustrates simulated reconstructions for single-scatter returns in accordance with an exemplary embodiment of the invention.

To demonstrate the expected noise variance spread in an exemplary imaging system, one can imagine a single column of voxels in the reconstruction volume aligned along the direction of the tagged photon flow. Approximately 324 single-scatter photons are available for radiographic imaging of each column of voxels, assuming a 20 millicurie source, a three-minute imaging time, a 2-meter standoff, and 1.5 cm cube voxels. FIG. 7 illustrates an example where 81 counts (left side) and 243 counts (right side) (totaling 324) have been reconstructed into a column of forty 1.5 cm voxels. Eighty-one counts represents the 25% single-scatter probability of 324 photons from 1 mm of body panel and the 243 counts represent the residual (from 324) remaining to scatter when encountering a radiographically-thick object. The reconstruction noise will spread over 40 channels because they represent the non-zero length of reconstruction kernel that a 2-nanosecond-range-gating precision implies.

The two plots shown in FIG. 7 simulate the reconstructed radiographic profile and expected noise for a single line of voxels that have imaged through a thin and a thick surface respectively in the target vehicle. We have plotted noise with a standard deviation equal to the square root of the counts on each channel and a central peak equal to the counts. Even with only 81 counts, the signal appears clearly above the noise.

Single-scatter coincident return photons can be assigned to the voxels around the inferred scattering location. However, for each return photon, the outgoing photon had to make it from the radioisotope source to the scattering site and the return photon back from the scattering site to the coded aperture detector. A maximum-likelihood reconstruction can be used to solve for a consistent radiographic density from the scattered photon data. The first image reconstruction step will simply be to populate a voxelized volume with the projected 3D locations of single scatter events. This essentially treats the photons from the source as a "spray paint" that has fallen through the imaging region and progressively deposited on the regions of radiographic density encountered. A second stage of reconstruction then takes this information and projects back to estimate both the flux irradiating this voxel from the source, and the probability that a scattered ray from this location makes it through the rest of the reconstruction region to the detector. This iterative approach will attempt to assign radiographic density correctly throughout the inspection volume, at least in regions with reasonable return scatter intensity.

Figure 8:
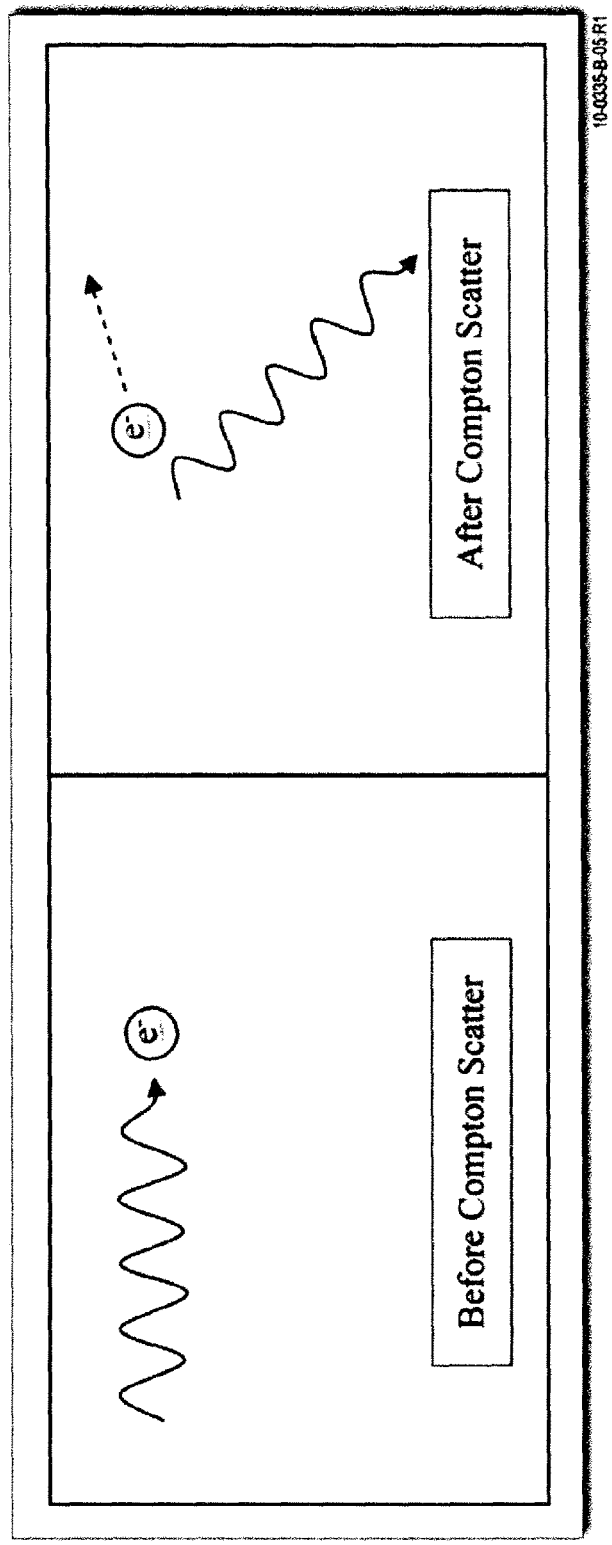
FIG. 8 illustrates Compton scattering of a photon from an electron in accordance with an exemplary embodiment of the invention.

Gamma and x-ray photons interact with matter almost exclusively by the mechanisms of photoelectric absorption, Compton scattering, and pair production. At the energy levels found with photons used in the exemplary imaging systems described in FIGS. 1 and 2, Compton scattering accounts for approximately 99% of the photon interactions. In Compton scattering, an incident photon interacts with an electron. Some energy and momentum of the incident photon transfer to the electron with the balance carried off in a scattered photon, as illustrated in FIG. 8. The incident photon's energy and angle of scatter determine the scattered photon's energy. The scattered photon's energy is given by $$E = 1/1 + \alpha(1 - \cos(\phi))$$

where the scattered photon's energy and the incident photon's energy are expressed in fractions of the rest mass energy of an electron $m_e c^2$. The photon's scattering angle from its incident direction is $\phi$. In the case of the exemplary embodiments described herein, the incident photon energy is $\alpha = 1$, or 511 keV. Photons of this energy that scatter by 90 degrees end up with exactly half this energy. The probability of scattering as a function of scattering angle is a well-defined function depending only on angle and energy.

Radiographic density for Compton scattering is determined by the density of electrons in the target material and the incident photon energy. The present exemplary embodiments of the invention can achieve good three-dimensional image resolution, while also given a 3-dimensional map of radiographic density to a depth of two or three voxels into a target with a density comparable to ammonium nitrate fuel oil (ANFO) explosives, namely 0.84 grams/cm³.

The imaging software module can use timing and energy data collected with respect to the outgoing probe photon and the backscattered return photon to identify single scatter photons for imaging reconstruction. Single scatter photons provide an image with improved contrast and reduced noise. The timing information collected for both the outgoing probe photons and the backscatter return photons allows the imaging software module to range-gate the total photon track length to a resolution of about 60 cm. From the known trajectory of the outgoing probe photon, the round trip time of flight of the detected backscattered return photon, and the position of the detector in the coded aperture imager registering a hit, the imaging software module can directly calculate the angle from which the photon has returned.

Figure 9:
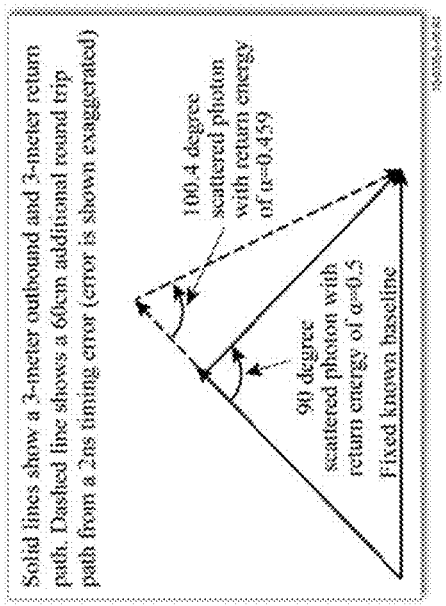
FIG. 9 illustrates the determination of scattering angle using timing information in accordance with an exemplary embodiment of the invention.

When a detector in the detector array registers a backscattered return photon, the distance between the source and the detector in the detector array can be calculated and is known as the baseline. The fixed known baseline is illustrated in FIG. 9. For example, assume a right-angle scatter where the source-to-scatter distance and the scatter-to-detector distance are both 3 meters as shown in FIG. 9. The source-to-detector baseline in this case is 3√2 meters. The return photon will have scattered by an angle of exactly 90 degrees and have exactly 50% of the outgoing 511 keV in energy (as shown by the Compton scattered photon energy formula in the previous section). Alternatively, as also illustrated in FIG. 9, if there is a two-nanosecond error in the time of flight measurement and the photon actually traveled a round-trip distance of 60 cm more, the angle of return of the backscattered photon is more acute—100.4 degrees—and the return energy of the scattered photon would be 8% lower—45.9% of 511 keV.

Figure 10:
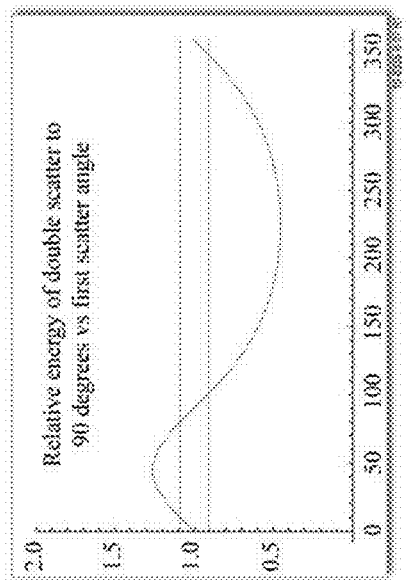
FIG. 10 illustrates energy bands for identifying single scatter events in accordance with an exemplary embodiment of the invention.

In view of these calculations illustrated in FIG. 9, the energy of single-scatter return photons can be predicted to an accuracy of approximately 8%. Photons outside of this energy range can be assumed to result from multiple scatterings or an accidental coincidence with a background event and therefore be rejected for purposes of the imaging. To determine what proportion of multiple scatter events should be rejected, FIG. 10 illustrates a simple calculation of the energy of a 511 keV photon after two sequential scatterings whose sum is 90 degrees. The horizontal axis is the first scattering angle. The vertical axis is the final photon energy, relative to that of a single 90-degree scatter (namely 256 keV). Superimposed on the illustration in FIG. 10 is an assumed 18% energy resolution on our return photon detection system. This is allocating 8% of uncertainty to the expected return photon energy and a 10% energy-resolution limit in the backscatter directional detector. Scatter events with an energy outside the two horizontal bands shown in FIG. 10 can be rejected as multiple scatter events. As illustrated in FIG. 10, if the first or the second scatter angle is zero, the resultant energy is that of a single scatter. Two consecutive 45-degree scatterings yield a maximum energy, while a first scatter of 90 degrees followed by a backscatter of 180 degrees yields a minimum. The plot shown in FIG. 10 is merely a first approximation because it only considers scattering in the plane and does not consider the cross-sections of the various scattering angles.

Referencing the reconstruction kernel discussed previously, an optimal kernel will use all of the available information to maximize the signal-to-noise ratio in the reconstruction. We have just discussed range gating and energy resolution to discriminate single-scatter from multiple scatter events. When addressing the reconstruction kernel previously, we applied range gating to limit the length of the outgoing photon track over which the coded aperture reconstruction kernel is applied, but did not incorporate energy information. Applying energy information, if the energy of the backscattered return photon is somewhat higher than the center energy that the range gating would imply, the coded aperture reconstruction kernel can be biased toward the lower scattering angle end to reconstruct this event. Similarly, lower energy events should bias the kernel to the higher end of its range. In this manner, the reconstruction uses all available information to reconstruct the image optimally.

The density of the target will determine the depth to which the probe photons can create an image of the target. Taking ANFO as a reference density, the probability that a photon travels some distance without interacting is $P_E(l)=\exp(-l/\lambda_E)$, where $\lambda_E$ is the expected length of travel for a photon of energy, E. This coefficient depends on energy and the electron density in the scattering material. For ANFO at 511 keV, $\lambda_E$ is 13.1 cm; a 90-degree scattered photon has an energy of 256 keV and $\lambda_E$ of 10.1 cm.

A single scatter photon must travel into the material of the target and back out without subsequent scattering. The probability that a photon makes it through a length l of material at 511 keV and then that length l again of material at 256 keV, the probability can be estimated by the product of the two probabilities:

$$P_{E1}(l) \times P_{E2}(l) = \exp(-l/\lambda_{E1}) \times \exp(-l/\lambda_{E2}) = \exp(-l(1/\lambda_{E1}+1/\lambda_{E2})).$$

The mean scattering lengths combine into a combined parameter, $1/\lambda_{tot}=(1/\lambda_{E1}+1/\lambda_{E2})$. The joint average length parameter is $1/(1/10.1+1/13.1)$ cm=5.7 cm. Assuming 45-degree entry and exit angles implies that we sample to a depth of $1/\sqrt{2}$ of 5.7 cm, which is 4.0 cm.

The foregoing calculation calculates the probability of traversal for entry and exit, assuming the exit angle is also 45 degrees. Additional simulations refine this and indicate that the average depth of single-scatter photons returning from a 45-degree angle of incidence is a depth of 3.4 cm in ANFO. Assuming a resolution of 1.5 cm, the image depth will include at least two voxels in a material with a density of ANFO and, consequently, will allow estimation of the radiographic volume density of the material.

To estimate expected count rates and backscatter return photon yields, we need estimates of the fraction of photons entering a thick target that exit via a single scatter. Simulations for 511 keV photons impacting a solid rectangular block of ANFO for various incidence angles are shown in the following table:

| Degrees | Single-Scatters in 100,000 | Single-Scatter Percent |
|---|---|---|
| 0 | 49,979 | 50.0% |
| 15 | 22,080 | 22.1% |
| 30 | 13,725 | 13.7% |
| 45 | 10,268 | 10.3% |
| 60 | 8,417 | 8.4% |
| 75 | 7,775 | 7.8% |
| 90 | 7,496 | 7.5% |

A positron annihilation source of 20 millicurie, with 3.7× $10^{10}$ disintegrations per curie and two photons per disintegration, yields a photon flux at 1 meter of $1.17 \times 10^5$ photons per $cm^2$ per second. We assume that the backscatter directional imaging detector (e.g., a coded aperture detector) has an area of 0.925 $m^2$ and is behind a coded aperture mask with a 50% open factor. If we assume the worst-case single-scatter-exit probability for a normal incidence of 7.5% and distribute this return flux uniformly over a 3-meter radius half sphere, we estimate that each square centimeter of target irradiated returns 144 single-scattered photons.

Each column of 1.5 cm voxels aligned toward the source is illuminated by $144 \times (1.5)^2 = 324$ photons. This is not large and would be inadequate for a general 3D volumetric reconstruction. However, much of the target is empty space. If 324 single-scatter return photons are available, falling through each voxel column and scattering on encountering material density, on average, once we've traversed to a depth of 3.4 cm AMFO density (assuming 45-degree entry and exit paths), we will have depleted the available single-scatter photons to a level of 1/e of the original flux. Those single-scatters we do detect are dispatched directly (on average) to the actual 3D location of their scattering. FIG. 7 offers an indication of how accurately we could reconstruct density in traversing a single line of voxels in which we had a return of 81 and 243 photons.

Background photons from other sources can affect the data collected at the backscatter imaging detector. However, the effect of these other background photons can be minimized by shielding the back and sides of the backscatter imaging detector. Measuring the timing and energy of the backscatter return photons also allows for identifying and filtering out background photons from the relevant data collected at the backscatter imaging detector.

Figure 11:
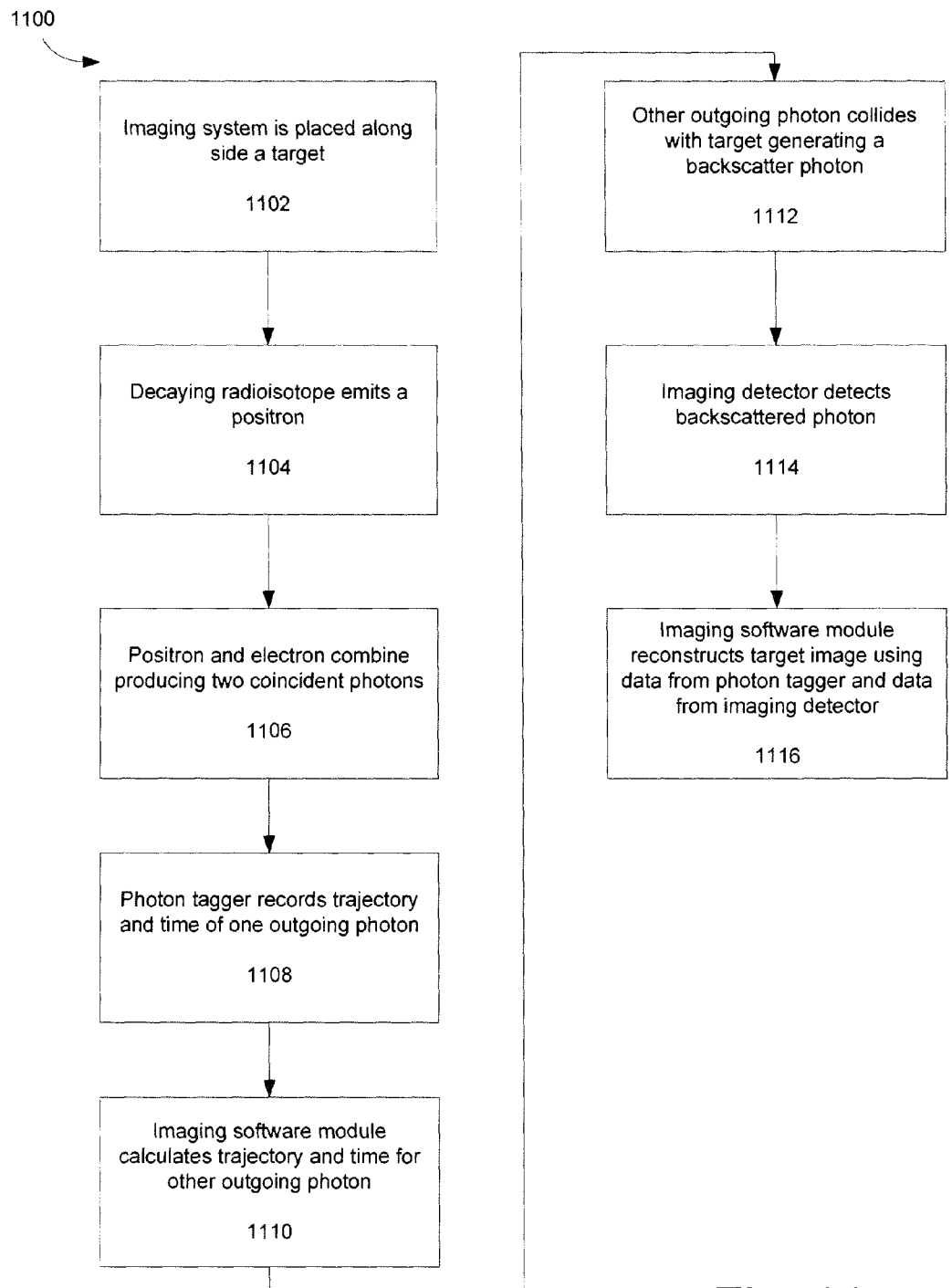
FIG. 11 illustrates a method for imaging a target using backscatter photons in accordance with an exemplary embodiment of the invention.

Referring now to FIG. 11, an exemplary method 1100 for performing imaging using annihilation coincidence photons is illustrated in accordance with one embodiment of the invention. Those of skill in the art will recognize that exemplary method 1100 is only one way to accomplish the invention and that alternate embodiments of the invention can involve adding steps to or removing steps from method 1100.

Exemplary method 1100 begins with step 1102 where the imaging system is placed along side a target. In the preferred embodiment, the imaging system is mounted in a vehicle that can drive up along side a variety of targets which can include other vehicles and other stationary objects. As described in step 1104, a decaying radioisotope source emits positrons. Although not required, typically, the decaying radioisotope source is placed inside a source holder that is part of the entire imaging system. The emitted positron collides with an electron annihilating the two particles and emitting two coincident photons traveling in opposite directions as referenced in step 1106. In the preferred embodiment, the annihilation occurs within the source holder.

In step 1108, one of the emitted photons is detected by a nearby photon tagger (also referred to as a gamma detector). The photon tagger is a commercially available piece of equipment that is able to determine the trajectory and an emission time for the detected photon. In step 1110, an imaging software module designed for processing the collected data calculates the trajectory and emission time for the other photon traveling in the opposite direction towards the target. The other photon traveling in the opposite direction away from the photon tagger collides with the target and generates a backscatter photon in step 1112. While there may be multiple collisions within the target, the preferred embodiment is primarily interested in photons that undergo only one scattering event with the target before being detected by an imaging detector.

In step 1114, the imaging detector detects the trajectory and timing associated with a backscattered photon when it collides with the imaging detector. A variety of imaging detectors can be used, but, as described above, the preferred embodiment implements a coded aperture imager. The imaging detector is typically part of the complete imaging system and can be positioned, for example, toward the rear of a vehicle as illustrated in FIG. 1. In step 1116, the imaging software module uses the data collected from the imaging detector and the data collected from the photon tagger for multiple photons and reconstructs the target image. The imaging software module can process a variety of collected data to reconstruct the target image. For example, in addition to the measured trajectories and measured times for the outgoing probe photon and the returning backscattered photon, the imaging software module can also use the measured energy level for the returning backscatter photon and the known energy of the outgoing probe photon.

The invention comprises computer programs, such as the exemplary imaging software module described above, that embody the functions described herein and that are illustrated in the appended flow charts. However, it should be apparent that there could be many different ways of implementing the imaging software module in computer programming, and the invention should not be construed as limited to any one set of computer program instructions. Further, a skilled programmer would be able to write such a computer program to implement an exemplary embodiment based on the flow charts and associated description in the application text. Therefore, disclosure of a particular set of program code instructions is not considered necessary for an adequate understanding of how to make and use the invention. The inventive functionality of the claimed computer program will be explained in more detail in the following description read in conjunction with the figures illustrating the program flow.

Figure 12:
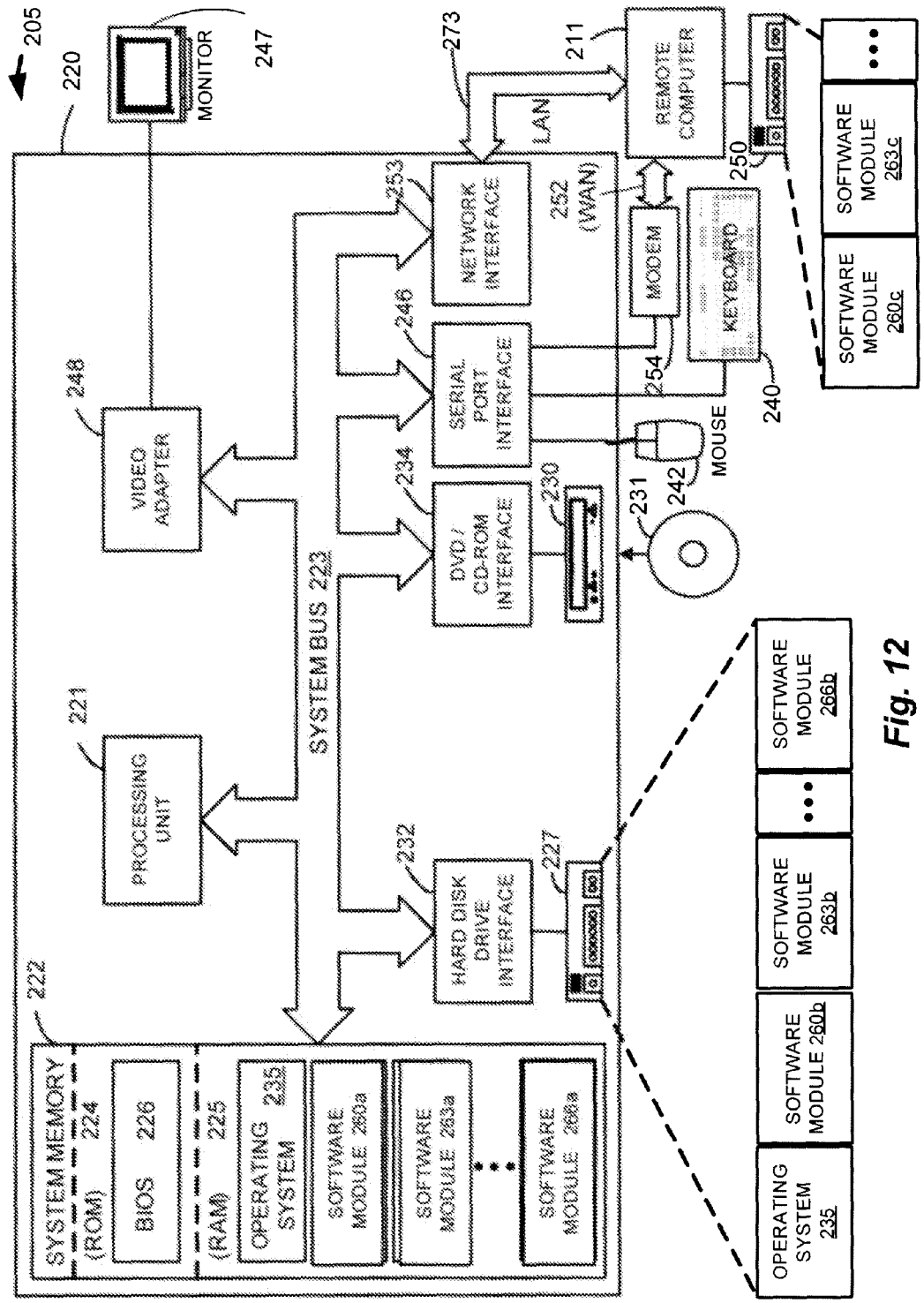
FIG. 12 illustrates a computing environment for executing an imaging software module in accordance with an exemplary embodiment of the invention.
Figure 3:
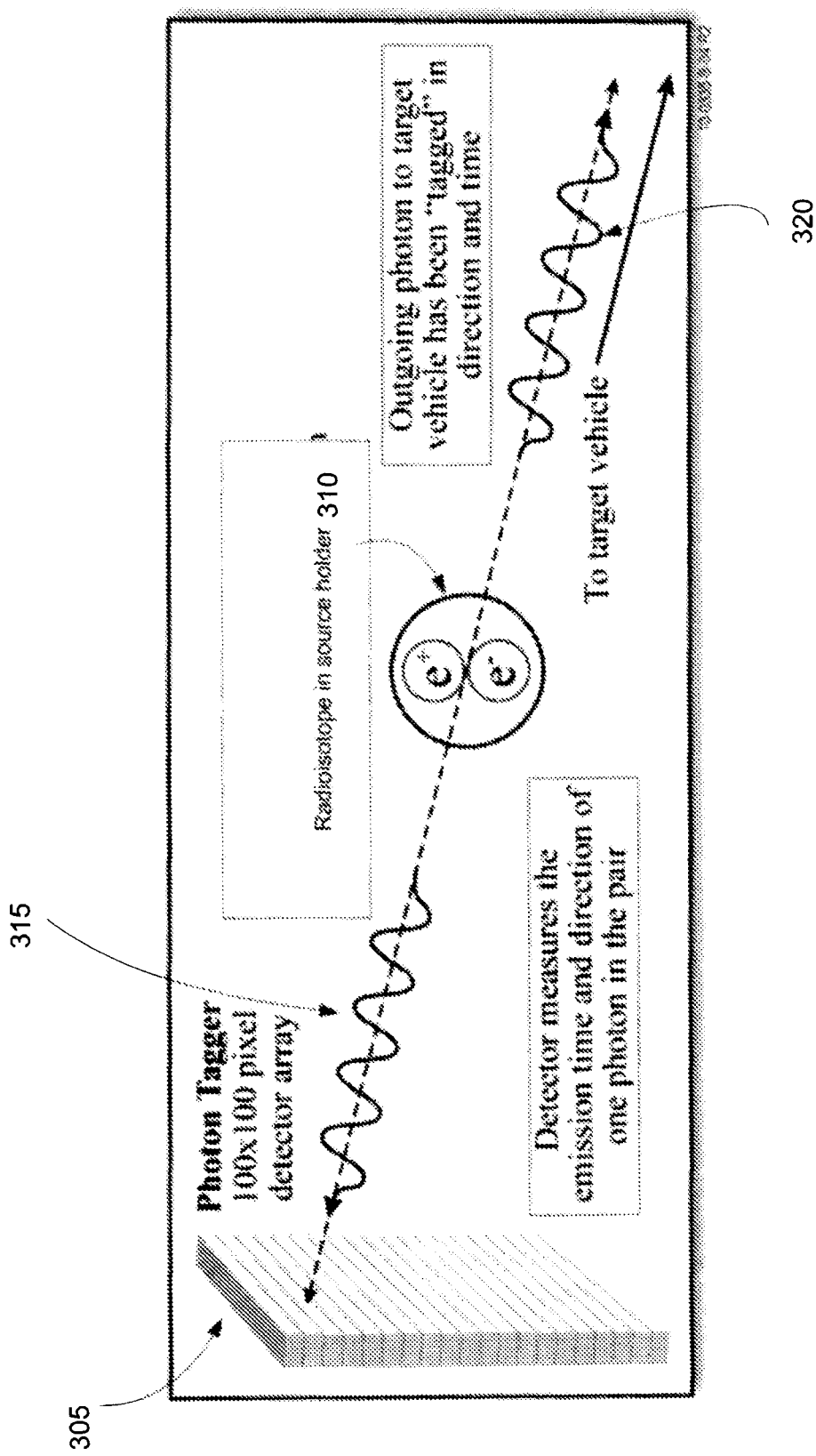

FIG. 12 illustrates a conventional computing device 220 suitable for supporting the operation of the imaging software module in the preferred embodiment of the present invention. The conventional computing device 220 can receive data from the photon tagger and the backscatter return photon detector via any one of a variety of conventional data communication links. In FIG. 12, the computing device 220 operates in a networked environment with logical connections to one or more remote computers 211. The logical connections between computing device 220 and remote computer 211 are represented by a local area network 273 and a wide area network 252. Those of ordinary skill in the art will recognize that in this client/server configuration, the remote computer 211 may function as a file server or computer server. Those of ordinary skill in the art also will recognize that the invention can function in a stand-alone computing environment.

The computing device 220 includes a processing unit 221, such as "PENTIUM" microprocessors manufactured by Intel Corporation of Santa Clara, Calif. The computing device 220 also includes system memory 222, including read only memory (ROM) 224 and random access memory (RAM) 225, which is connected to the processor 221 by a system bus 223. The preferred computing device 220 utilizes a BIOS 226, which is stored in ROM 224. Those skilled in the art will recognize that the BIOS 226 is a set of basic routines that helps to transfer information between elements within the computing device 220. Those skilled in the art will also appreciate that the present invention may be implemented on computers having other architectures, such as computers that do not use a BIOS, and those that utilize other microprocessors.

Within the computing device 220, a local hard disk drive 227 is connected to the system bus 223 via a hard disk drive interface 232. A CD-ROM or DVD drive 230, which is used to read a CD-ROM or DVD disk 231, is connected to the system bus 223 via a CD-ROM or DVD interface 234. In other embodiments, other types of storage devices such as external hard disk drives and USB thumb drives can be used. A user enters commands and information into the computing device 220 by using input devices, such as a keyboard 240 and/or pointing device, such as a mouse 242, which are connected to the system bus 223 via a serial port interface 246. Other types of pointing devices (not shown in FIG. 12) include track pads, track balls, pens, head trackers, data gloves and other devices suitable for positioning a cursor on a computer monitor 247. The monitor 247 or other kind of display device is connected to the system bus 223 via a video adapter 248.

The remote computer 211 in this networked environment is connected to a remote memory storage device 250. This remote memory storage device 250 is typically a large capacity device such as a hard disk drive, CD-ROM or DVD drive, magneto-optical drive or the like. Those skilled in the art will understand that software modules are provided to the remote computer 211 via computer-readable media. The computing device 220 is connected to the remote computer by a network interface 153, which is used to communicate over the local area network 173.

In an alternative embodiment, the computing device 220 is also connected to the remote computer 211 by a modem 254, which is used to communicate over the wide area network 252, such as the Internet. The modem 254 is connected to the system bus 223 via the serial port interface 246. The modem 254 also can be connected to the public switched telephone network (PSTN) or community antenna television (CATV) network. Although illustrated in FIG. 12 as external to the computing device 220, those of ordinary skill in the art can recognize that the modem 254 may also be internal to the computing device 220, thus communicating directly via the system bus 223. Connection to the remote computer 211 via both the local area network 273 and the wide area network 252 is not required, but merely illustrates alternative methods of providing a communication path between the computing device 220 and the remote computer 211.

Although other internal components of the computing device 220 are not shown, those of ordinary skill in the art will appreciate that such components and the interconnection between them are well known. Accordingly, additional details concerning the internal construction of the computing device 220 need not be disclosed in connection with the present invention.

Those skilled in the art will understand that program modules, such as an operating system 235 and other software modules 260*a*, 263*a* and 266*a*, and data are provided to the computing device 220 via computer-readable media. In the preferred computing device, the computer-readable media include local or remote memory storage devices, which may include the local hard disk drive 227, CD-ROM or DVD 231, RAM 225, ROM 224, and the remote memory storage device 250.

In conclusion, the invention, as represented in the foregoing exemplary embodiments, provides systems and methods for imaging a target object using coincident photons created during an electron-positron annihilation. As described in the foregoing exemplary embodiments, the trajectory and timing of the photons can be used track the photons as they collide with a target and create backscattered photons that are detected and used to create an image of the target.

The embodiments set forth herein are intended to be exemplary. From the description of the exemplary embodiments, equivalents of the elements shown herein and ways of constructing other embodiments of the invention will be apparent to practitioners of the art. For example, while the components of the imaging system are located together in a vehicle in the preferred embodiment, in other embodiments the components can be separated or located at different positions around the target. Similarly, in other embodiments the imaging software module can perform different types of analyses to either consider or filter return photons that undergo multiple scattering collisions. Many other modifications, features and embodiments of the invention will become evident to those of skill in the art. It should be appreciated, therefore, that many aspects of the invention were described above by way of example only and are not intended as required or essential elements of the invention unless explicitly stated otherwise. Accordingly, it should be understood that the foregoing relates only to certain embodiments of the invention and that numerous changes can be made therein without departing from the spirit and scope of the invention.

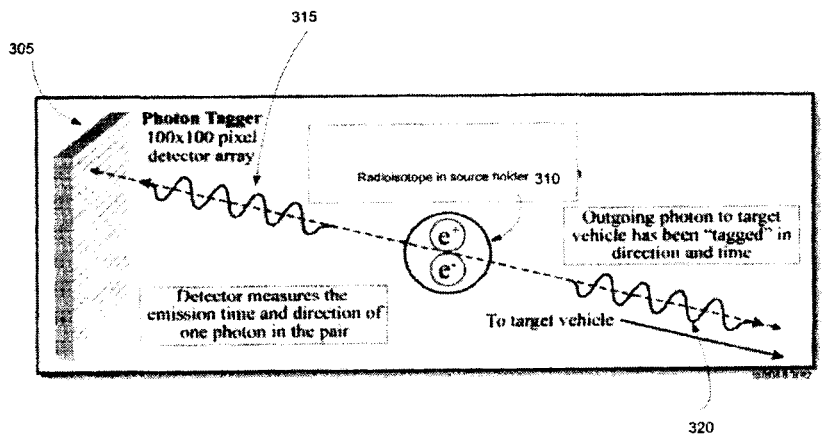

We claim:

1. A method for creating an image of a target, the method comprising:
    emitting positrons from a first location that collide with electrons at the first location, wherein each collision results in the emission of a first photon and a second photon;
    intercepting by a first detector at least a portion of the emitted first photons and measuring a first trajectory and a first time associated with each of the intercepted first photons based on at least the first location;
    calculating by an imaging software module installed on a computer a second time and a second trajectory associated with each of at least a portion of the second photons in accordance with the measured first trajectories and a first times associated with each of the intercepted first photons;
    receiving at an imaging detector multiple photons and generating scatter energy and scatter time data for each of the multiple photons, wherein a least a portion of the multiple photons are single-scatter photons resulting from a single collision between a second photon and the target;
    filtering by the imaging software module the multiple photons using the scatter energy and scatter time data to identify and retain the single-scatter photons for imaging;
    calculating by the imaging software module a scatter trajectory and a scatter time associated with each of the retained single-scatter photons;
    calculating by the imaging software module multiple positions within the target based on the second times, the second trajectories, the scatter times and the scatter trajectories; and
    creating by the imaging software module a three-dimensional image of the target using at least the calculated multiple positions.

2. The method of claim 1, wherein the imaging detector is a coded aperture imager comprising an array of detectors and a patterned mask.

3. The method of claim 1, wherein the radioisotope source and the imaging detector are located on a same side of the target.

4. The method of claim 1, wherein filtering utilizes trajectory and energy information for each of the received multiple photons.

5. The method of claim 1, wherein the first detector is a gamma detector.

6. A system for creating an image of a target, the system comprising:
    a positron source and an approximately co-located electron source for facilitating collisions between positrons and electrons in a first location, wherein each collision produces a first photon and a second photon;
    a photon detector for intercepting at least a portion of the emitted first photons and measuring a first trajectory and a first time associated with each of the intercepted first photons based on at least the first location;
    an imaging software module installed on a computer, the imaging software module calculating a second trajectory and a second time associated with each second photon in accordance with the measured first trajectory and first time associated with each of the intercepted first photons;
    an imaging detector receiving multiple photons therein, wherein a least a portion of the multiple photons are single-scatter photons resulting from a single collision between a second photon and the target, and measuring a scatter energy and a scatter time associated with each of the multiple photons; and
    wherein the imaging software module:
        filters the multiple photons using the scatter energies and scatter times to identify and retain for target imaging the single-scatter photons;
        calculates a scatter trajectory and a scatter time associated with each of the retained single-scatter photons;
        calculates multiple positions within the target based on the second times, the second trajectories, the scatter times and the scattered trajectories; and
        creates a three-dimensional image of the target using at least the calculated multiple positions.

7. The system of claim 6, wherein the imaging detector comprises shielding to reduce a number of background photons that reach the imaging detector.

8. The system of claim 6, wherein the detector is a coded aperture imager comprising an array of detectors and a patterned mask.

9. The system of claim 6, wherein the positron and electron sources and the imaging detector are located on a same side of the target.

10. The system of claim 6, wherein the filtering utilizes trajectory and energy information for each of the received multiple photons.

11. The system of claim 6, further comprising a source holder for containing the positron source, wherein the source holder comprises a first window for emitting the first photon and a second window for emitting the second photon.

12. The system of claim 6, wherein the first window further comprises a collimator to direct the second photons towards the target.

13. The system of claim 6, wherein the positron source, the electron source, the photon detector, the imaging software module and the imaging detector are located on a single platform.

14. The system of claim 13, wherein the single platform is movable.

15. The system of claim 6, wherein the positron source is a radioisotope source.

16. A computer program product comprising an imaging software module stored on a non-transitory computer-readable medium, the imaging software module comprising:

instructions for receiving from a photon detector measured pairs of first trajectories and first times associated with individual intercepted first photons, each of the first photons being part of a photon pair generated from a collision between a positron and an electron;

instructions for calculating pairs of second times and a second trajectories associated with each of second photons resulting from collisions in accordance with the measured pairs of first trajectories and a first times associated with each of the intercepted first photons;

instructions for receiving from an imaging detector pairs of scatter energies and scatter times associated with each of multiple photons received thereby, at least a portion of the multiple photons being single-scatter photons resulting from collisions between each of the second photons and a target;

instructions for filtering the multiple photons using the scatter energies and scatter times to identify and retain for target imaging the single-scatter photons;

instructions for calculating a scatter trajectory and a scatter time associated with each of the retained single-scatter photons;

instructions for calculating multiple positions within the target based on the second times, the second trajectories, the scatter times and the scatter trajectories; and instructions for creating a three-dimensional image of the target using at least the calculated multiple positions.

* * * * *

UNITED STATES PATENT AND TRADEMARK OFFICE
CERTIFICATE OF CORRECTION

PATENT NO. : 8,426,822 B1
APPLICATION NO. : 13/646920
DATED : April 23, 2013
INVENTOR(S) : Penny et al.

Page 1 of 3

It is certified that error appears in the above-identified patent and that said Letters Patent is hereby corrected as shown below:

The Title page, showing the illustrative figure, should be deleted and substitute therefor the attached Title page.

In the Drawings:

Delete fig. 3 and substitute therefor the drawing sheet, consisting of fig. 3 as shown on the attached page.

Signed and Sealed this
Twenty-third Day of July, 2013

Teresa Stanek Rea
*Acting Director of the United States Patent and Trademark Office*

CERTIFICATE OF CORRECTION (continued)

(12) United States Patent
Penny et al.

(10) Patent No.: US 8,426,822 B1
(45) Date of Patent: Apr. 23, 2013

(54) SYSTEM AND METHOD FOR THREE-DIMENSIONAL IMAGING USING SCATTERING FROM ANNIHILATION COINCIDENCE PHOTONS

(71) Applicants: Robert David Penny, San Diego, CA (US); John D. Valentine, San Diego, CA (US)

(72) Inventors: Robert David Penny, San Diego, CA (US); John D. Valentine, San Diego, CA (US)

(73) Assignee: Science Application International Corporation, McLean, VA (US)

( * ) Notice: Subject to any disclaimer, the term of this patent is extended or adjusted under 35 U.S.C. 154(b) by 0 days.

(21) Appl. No.: 13/646,920

(22) Filed: Oct. 8, 2012

Related U.S. Application Data

(63) Continuation of application No. 12/939,449, filed on Nov. 4, 2010, now Pat. No. 8,314,394.

(60) Provisional application No. 61/257,874, filed on Nov. 4, 2009.

(51) Int. Cl.
*G01T 1/164* (2006.01)

(52) U.S. Cl.
USPC .................................................. 250/363.03

(58) Field of Classification Search ............. 250/362, 250/363.01–363.1
See application file for complete search history.

(56) References Cited

U.S. PATENT DOCUMENTS

| | | | |
|---|---|---|---|
| 3,124,679 A | 3/1964 | Tittman et al. | 250/43.5 |
| 3,240,971 A | 3/1966 | Morgan | 376/153 |
| 3,390,269 A | 6/1968 | Packard | 250/328 |
| 3,670,164 A | 6/1972 | Hardy et al. | 250/366 |
| 3,780,291 A | 12/1973 | Stein et al. | 250/363 |
| 3,784,827 A | 1/1974 | Calhoun | 250/106 S |
| 3,790,785 A | 2/1974 | Paolini et al. | 250/71.5 R |
| 3,808,444 A | 4/1974 | Schneeberger et al. | 250/492 |
| 3,829,695 A | 8/1974 | Powell | 250/358.1 |
| 3,835,324 A | 9/1974 | Weigle | 250/360 |
| 3,984,332 A | 10/1976 | Nelson et al. | 250/368 |

(Continued)

FOREIGN PATENT DOCUMENTS

| EP | 0 059 382 | 8/1985 |
|---|---|---|
| EP | 0 491 977 | 6/1994 |

(Continued)

OTHER PUBLICATIONS

U.S. Appl. No. 90/005,268, filed Feb. 19, 1999.

(Continued)

*Primary Examiner* — Kiho Kim
(74) *Attorney, Agent, or Firm* — King & Spaulding LLP

(57) ABSTRACT

Systems and methods are described herein for performing three-dimensional imaging using backscattered photons generated from a positron-electron annihilation. The systems and methods are implemented using the pair of photons created from a positron-electron annihilation. The trajectory and emission time of one of the photons is detected near the annihilation event. Using this collected data, the trajectory of the second photon can be determined. The second photon is used as a probe photon and is directed towards a target for imaging. The interaction of the second probe photon with the target produces back scattered photons that can be detected and used to create a three-dimensional image of the target. The systems and methods described herein are particularly advantageous because they permit imaging with a system from a single side of the target, as opposed to requiring imaging equipment on both sides of the target.

16 Claims, 10 Drawing Sheets